(12) United States Patent
Fuselier et al.

(10) Patent No.: US 12,377,157 B2
(45) Date of Patent: Aug. 5, 2025

(54) CONJUGATES, THEIR COMPOSITIONS, AND THEIR RELATED METHODS

(71) Applicant: THE ADMINISTRATORS OF THE TULANE EDUCATIONAL FUND, New Orleans, LA (US)

(72) Inventors: Joseph A. Fuselier, New Orleans, LA (US); David H. Coy, New Orleans, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 0 days.

(21) Appl. No.: 18/714,111

(22) PCT Filed: Dec. 14, 2022

(86) PCT No.: PCT/US2022/081579
§ 371 (c)(1),
(2) Date: May 29, 2024

(87) PCT Pub. No.: WO2023/114861
PCT Pub. Date: Jun. 22, 2023

(65) Prior Publication Data
US 2025/0121080 A1    Apr. 17, 2025

Related U.S. Application Data

(60) Provisional application No. 63/265,421, filed on Dec. 15, 2021.

(51) Int. Cl.
*A61K 9/19* (2006.01)
*A61K 47/64* (2017.01)
*A61P 35/00* (2006.01)

(52) U.S. Cl.
CPC .............. *A61K 47/643* (2017.08); *A61K 9/19* (2013.01); *A61P 35/00* (2018.01)

(58) Field of Classification Search
CPC .......... A61K 47/643; A61K 9/19; A61P 35/00
See application file for complete search history.

(56) References Cited

U.S. PATENT DOCUMENTS

| | | | |
|---|---|---|---|
| 4,424,219 A | 1/1984 | Hashimoto et al. | |
| 4,554,101 A | 11/1985 | Hopp | |
| 2011/0059076 A1* | 3/2011 | McDonagh | C07K 16/40 514/274 |

FOREIGN PATENT DOCUMENTS

| | | |
|---|---|---|
| WO | 2009/126920 A2 | 10/2009 |
| WO | 2009/134952 A2 | 11/2009 |

(Continued)

OTHER PUBLICATIONS

International Search Report from PCT/US2022/081579, mailed Apr. 17, 2023, 4 pages.

(Continued)

*Primary Examiner* — Joseph K McKane
*Assistant Examiner* — Jalisa Holmes Ferguson
(74) *Attorney, Agent, or Firm* — ALGM LLP; Harry J. Guttman

(57) ABSTRACT

Some embodiments of the invention include inventive compounds (e.g., compounds of Formula (I)). Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inven- (Continued)

tive compound. Additional embodiments of the invention are also discussed herein.

32 Claims, 14 Drawing Sheets

(56) References Cited

FOREIGN PATENT DOCUMENTS

WO  2018/026742 A1  2/2018
WO  2019/108975 A1  6/2019

OTHER PUBLICATIONS

Written Opinion from PCT/US2022/081579, mailed Apr. 17, 2023, 5 pages.
Andreu et al. (1994) "Formation of Disulfide Bonds in Synthetic Peptides and Proteins" from Methods in Molecular Biology, vol. 35: Peptide Synthesis Protocols, Edited by: M. W. Pennington and B. M. Dunn, Humana Press Inc., Totowa, NJ.
Beck et al. (2004) "Direct observation of covalent adducts with Cys34 of human serum albumin using mass spectrometry" Analytical Biochemistry, vol. 325, pp. 326-336.
Costantino et al. (1995) "Aggregation of a Lyophilized Pharmaceutical Protein, Recombinant Human Albumin: Effect of Moisture and Stabilization by Excipients" Nature Biotechnology, vol. 13, pp. 493-496.
Fotouhi et al. (1989) "Peptide Synthesis by Prior Thiol Capture. 6. Rates of the Disulfide Bond Forming Capture Reaction and Demonstration of the Overall Strategy by Synthesis of the C-Terminal 29-Peptide Sequence of BPTI" J. Org. Chem., vol. 54, pp. 2803-2817.
Han et al. (2007) "Effects of Sugar Additives on Protein Stability of Recombinant Human Serum Albumin during Lyophilization and Storage" Arch Pharm Res, vol. 30, No. 9, pp. 1124-1131.
Hapuarachchige et al. (2020) "Cellular Delivery of Bioorthogonal Pretargeting Therapeutics in PSMA-Positive Prostate Cancer" Mol. Pharmaceutics, vol. 17, pp. 98-108.
Hoogenboezem et al. (2018) "Harnessing albumin as a carrier for cancer therapies" Advanced Drug Delivery Reviews, vol. 130, pp. 73-89.
Khodade et al. (2018) "Development of S-Substituted Thioisothioureas as Efficient Hydropersulfide Precursors" J. Am. Chem. Soc., vol. 140, pp. 17333-17337.
Kratz (2008) "Albumin as a drug carrier: Design of prodrugs, drug conjugates and nanoparticles" Journal of Controlled Release, vol. 132, pp. 171-183.
Kyte et al. (1982) "A Simple Method for Displaying the Hydropathic Character of a Protein" J. Mol. Biol., vol. 157, pp. 105-132.
Pillow et al. (2017) "Decoupling stability and release in disulfide bonds with antibody-small molecule conjugates" Chemical Science, vol. 8, No. 1, pp. 366-370.
Reubi (2007) "Peptide receptor expression in GEP-NET" Virchows Arch, vol. 451 (Suppl 1), pp. S47-S50.
Sadowsky et al. (2017) "Development of Efficient Chemistry to Generate Site-Specific Disulfide-Linked Protein- and Peptide-Payload Conjugates: Application to THIOMAB Antibody-Drug Conjugates" Bioconjugate Chem., vol. 28, pp. 2086-2098 (plus Supporting Information).
Steglich et al. (2020) "Expression, purification and initial characterization of human serum albumin domain I and its cysteine 34" PLoS One, vol. 15, No. 10, Article e0240580 (15 pages).
Su et al. (2018) "Modulating Antibody-Drug Conjugate Payload Metabolism by Conjugation Site and Linker Modification" Bioconjugate Chem., vol. 29, pp. 1155-1167.
Summa et al. (2007) "Protein-thiol substitution or protein dethiolation by thiol/disulfide exchange reactions: The albumin model" Proteins, vol. 69, pp. 369-378.
Wasilewska et al. (2019) "Human Serum Albumin Adsorption Kinetics on Silica: Influence of Protein Solution Stability" Langmuir, vol. 35, pp. 2639-2648.
White (2013) "Exploiting the bad eating habits of Ras-driven cancers" Genes & Development, vol. 27, pp. 2065-2071.
Worm et al.(2020) "Targeting of peptide-binding receptors on cancer cells with peptide-drug conjugates" Peptide Science, vol. 112, Article e24171 (22 pages).

\* cited by examiner

CONJUGATES, THEIR COMPOSITIONS, AND THEIR RELATED METHODS

CROSS-REFERENCE TO RELATED APPLICATIONS

This application is a National Stage Entry of International Application No. PCT/US2022/081579 filed Dec. 14, 2022, entitled "CONJUGATES, THEIR COMPOSITIONS, AND THEIR RELATED METHODS" which is herein incorporated by reference in its entirety, and which claims the benefit of U.S. Provisional Application No. 63/265,421, filed Dec. 15, 2021, entitled "CONJUGATES, THEIR COMPOSITIONS, AND THEIR RELATED METHODS", which is herein incorporated by reference in its entirety.

BACKGROUND

Some compounds (e.g., inhibitors and/or macrocyclic compounds) have potential anti-cancer activity and/or anti-tumor activity. Some of these compounds can be toxic to normal (e.g., non-cancer) animal cells, and are sometimes ineffective at tolerable doses. There remains a broad need to develop new compounds that treat cancer in animals. Certain embodiments of the invention can address one or more of the deficiencies discussed above.

Some embodiments of the invention include inventive compounds (e.g., compounds of Formula (I)). Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound. Additional embodiments of the invention are also discussed herein.

SUMMARY

Some embodiments of the present invention include a compound selected from Formula (I)

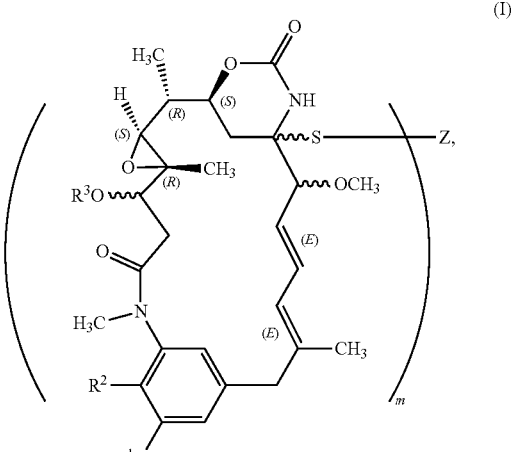

(I)

salts, optical isomers, geometric isomers, salts of isomers, and derivatives thereof. In certain embodiments, $R^1$ is selected from H, —COCH$_3$, carboxy (—CO$_2$H), ethynyl (—CCH), $C_1$-$C_8$ alkyl, $C_2$-$C_8$ alkenyl, $C_2$-$C_8$ alkynyl, methyl, ethyl, perfluorinated methyl, perfluorinated ethyl, $C_1$-$C_4$ alkylsulfonyl (—S(=O)$_2$—($C_1$-$C_4$ alkyl)), and phenyl-($C_1$-$C_4$ alkyl), which —COCH$_3$, carboxy (—CO$_2$H), ethynyl (—CCH), $C_1$-$C_8$ alkyl, $C_2$-$C_8$ alkenyl, $C_2$-$C_8$ alkynyl, methyl, ethyl, $C_1$-$C_4$ alkylsulfonyl, or phenyl-($C_1$-$C_4$ alkyl) can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, phenyl, perfluorinated methyl, perfluorinated ethyl, amino, $C_1$-$C_4$ alkanoylamino (—NH—CO—($C_1$-$C_4$ alkyl)), $C_1$-$C_4$ alkoxy, benzyloxy (—O—CH$_2$-phenyl), oxo (=O), $C_2$-$C_5$ alkoxycarbonyl (—CO—O—($C_2$-$C_5$ alkyl)), methylenedioxy (—O—CH$_2$—O—, with one or two attachment carbons), or $C_1$-$C_4$ alkylthio (—S—($C_1$-$C_4$ alkyl)). In other embodiments, $R^2$ is selected from H, allyl, vinyl, hydroxyl, Cl, Br, F, I, thiol, amino, nitro, cyano, $C_1$-$C_4$ alkyl, $C_1$-$C_4$ alkylnoic, phenyl, $C_1$-$C_2$ perfluorinated alkyl, alkyl amino, oxo, carboxy, acetyl, amido, and $C_1$-$C_3$ alkoxy. In some embodiments, $R^3$ is selected from H, $C_1$-$C_{18}$ alkyl, $C_2$-$C_{20}$ alkenyl, $C_2$-$C_{20}$ alkynyl, methyl, ethyl, perfluorinated methyl, perfluorinated ethyl, aryl, cycloalkyl, and —COR$^4$, which $C_1$-$C_{18}$ alkyl, $C_2$-$C_{20}$ alkenyl, $C_2$-$C_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$—($C_1$-$C_4$ alkyl)), oxo (=O), thioxo (=S), or $C_1$-$C_4$ alkanoylamino (—CO—NH—($C_1$-$C_4$ alkyl)). In yet other embodiments, $R^4$ is selected from $C_1$-$C_{18}$ alkyl, $C_2$-$C_{20}$ alkenyl, $C_2$-$C_{20}$ alkynyl, methyl, ethyl, perfluorinated methyl, perfluorinated ethyl, aryl, cycloalkyl, and

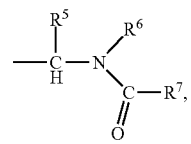

which $C_1$-$C_{18}$ alkyl, $C_2$-$C_{20}$ alkenyl, $C_2$-$C_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$—($C_1$-$C_4$ alkyl)), oxo (=O), thioxo (=S), or $C_1$-$C_4$ alkanoylamino (—CO—NH—($C_1$-$C_4$ alkyl)). In still other embodiments, $R^5$, $R^6$, and $R^7$ are the same or different and each is independently selected from $C_1$-$C_{18}$ alkyl, $C_2$-$C_{20}$ alkenyl, $C_2$-$C_{20}$ alkynyl, methyl, ethyl, perfluorinated methyl, perfluorinated ethyl, aryl, and cycloalkyl, which $C_1$-$C_{18}$ alkyl, $C_2$-$C_{20}$ alkenyl, $C_2$-$C_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, C$_1$-C$_4$ alkoxy, C$_2$-C$_4$ alkanoyl (—CO—(C$_2$-C$_4$ alkyl)), C$_2$-C$_4$ alkanoyloxy (—CO—O—(C$_2$-C$_4$ alkyl)), C$_2$-C$_4$ alkoxycarbonyl (—O—CO—(C$_2$-C$_4$ alkyl)), nitro, amino, mono(C$_1$-C$_4$ alkyl)amino, di(C$_1$-C$_4$ alkyl)amino, C$_1$-C$_4$ alkylthio (—S—(C$_1$-C$_4$ alkyl)), C$_1$-C$_4$ alkylsulfinyl (—SO—(C$_1$-C$_4$ alkyl)), C$_1$-C$_4$ alkylsulfonyl (—S(=O)$_2$—(C$_1$-C$_4$ alkyl)), oxo (=O), thioxo (=S), or C$_1$-C$_4$ alkanoylamino (—CO—NH—(C$_1$-C$_4$ alkyl)). In certain embodiments, m is 1, 2, 3, 4, 5, 6, 7, 8, 9, or 10. In some embodiments, Z is selected from an albumin, human serum albumin (HSA), bovine serum albumin (BSA), canine serum albumin (CSA), feline serum albumin (FSA), equine serum albumin (ESA), Domain I of HSA, Domain II of HSA, Domain III of HSA, an engineered albumin, mutants thereof, and fragments thereof.

In other embodiments, R$^1$ is selected from H, —COCH$_3$, carboxy (—CO$_2$H), ethynyl (—CCH), C$_1$-C$_4$ alkyl, C$_2$-C$_4$ alkenyl, C$_2$-C$_4$ alkynyl, methyl, ethyl, perfluorinated methyl, and perfluorinated ethyl, which —COCH$_3$, carboxy (—CO$_2$H), ethynyl (—CCH), C$_1$-C$_4$ alkyl, C$_2$-C$_4$ alkenyl, C$_2$-C$_4$ alkynyl, methyl, or ethyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, amino, C$_1$-C$_4$ alkoxy, or oxo. In some embodiments, R$^1$ is selected from the group consisting of H, —COCH$_3$, carboxy (—CO$_2$H), ethynyl (—CCH), methyl, ethyl, perfluorinated methyl, and perfluorinated ethyl.

In yet other embodiments, R$^2$ is selected from the group consisting of H, Cl, Br, F, I, allyl, ethyl, methyl, and OH. In still other embodiments, R$^2$ is H or Cl.

In other embodiments, R$^3$ is selected from the group consisting of methyl, ethyl, propyl, butyl, pentyl, hexyl, heptyl, octyl, and nonyl. In certain embodiments, R$^3$ is

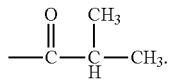

In some embodiments, R$^3$ is

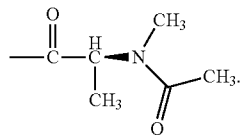

In yet other embodiments, R$^4$ is selected from C$_1$-C$_{18}$ alkyl, C$_2$-C$_{20}$ alkenyl, C$_2$-C$_{20}$ alkynyl, methyl, ethyl, perfluorinated methyl, perfluorinated ethyl, aryl, and cycloalkyl, which C$_1$-C$_{18}$ alkyl, C$_2$-C$_{20}$ alkenyl, C$_2$-C$_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, C$_1$-C$_4$ alkoxy, C$_2$-C$_4$ alkanoyl (—CO—(C$_2$-C$_4$ alkyl)), C$_2$-C$_4$ alkanoyloxy (—CO—O—(C$_2$-C$_4$ alkyl)), C$_2$-C$_4$ alkoxycarbonyl (—O—CO—(C$_2$-C$_4$ alkyl)), nitro, amino, mono(C$_1$-C$_4$ alkyl)amino, di(C$_1$-C$_4$ alkyl)amino, C$_1$-C$_4$ alkylthio (—S—(C$_1$-C$_4$ alkyl)), C$_1$-C$_4$ alkylsulfinyl (—SO—(C$_1$-C$_4$ alkyl)), C$_1$-C$_4$ alkylsulfonyl (—S(=O)$_2$—(C$_1$-C$_4$ alkyl)), oxo (=O), thioxo (=S), or C$_1$-C$_4$ alkanoylamino (—CO—NH—(C$_1$-C$_4$ alkyl)). In some embodiments, R$^4$ is selected from C$_1$-C$_{10}$ alkyl, C$_2$-C$_{10}$ alkenyl, C$_2$-C$_{10}$ alkynyl, methyl, ethyl, perfluorinated methyl, and perfluorinated ethyl, which C$_1$-C$_{10}$ alkyl, C$_2$-C$_{10}$ alkenyl, C$_2$-C$_{10}$ alkynyl, methyl, or ethyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, C$_1$-C$_4$ alkoxy, C$_2$-C$_4$ alkanoyl (—CO—(C$_2$-C$_4$ alkyl)), C$_2$-C$_4$ alkanoyloxy (—CO—O—(C$_2$-C$_4$ alkyl)), C$_2$-C$_4$ alkoxycarbonyl (—O—CO—(C$_2$-C$_4$ alkyl)), nitro, amino, mono(C$_1$-C$_4$ alkyl)amino, di(C$_1$-C$_4$ alkyl)amino, C$_1$-C$_4$ alkylthio (—S—(C$_1$-C$_4$ alkyl)), C$_1$-C$_4$ alkylsulfinyl (—SO—(C$_1$-C$_4$ alkyl)), C$_1$-C$_4$ alkylsulfonyl (—S(=O)$_2$—(C$_1$-C$_4$ alkyl)), oxo (=O), thioxo (=S), or C$_1$-C$_4$ alkanoylamino (—CO—NH—(C$_1$-C$_4$ alkyl)). In certain embodiments, R$^4$ is selected from the group consisting of methyl, ethyl, propyl, butyl, pentyl, and hexyl. In other embodiments, R$^4$ is

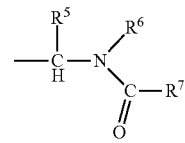

and R$^5$, R$^6$, and R$^7$ are the same or different and each is independently selected from C$_1$-C$_{18}$ alkyl, C$_2$-C$_{20}$ alkenyl, C$_2$-C$_{20}$ alkynyl, methyl, ethyl, perfluorinated methyl, and perfluorinated ethyl, which C$_1$-C$_{18}$ alkyl, C$_2$-C$_{20}$ alkenyl, C$_2$-C$_{20}$ alkynyl, methyl, or ethyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, C$_1$-C$_4$ alkoxy, C$_2$-C$_4$ alkanoyl (—CO—(C$_2$-C$_4$ alkyl)), C$_2$-C$_4$ alkanoyloxy (—CO—O—(C$_2$-C$_4$ alkyl)), C$_2$-C$_4$ alkoxycarbonyl (—O—CO—(C$_2$-C$_4$ alkyl)), nitro, amino, mono(C$_1$-C$_4$ alkyl)amino, di(C$_1$-C$_4$ alkyl)amino, C$_1$-C$_4$ alkylthio (—S—(C$_1$-C$_4$ alkyl)), C$_1$-C$_4$ alkylsulfinyl (—SO—(C$_1$-C$_4$ alkyl)), C$_1$-C$_4$ alkylsulfonyl (—S(=O)$_2$—(C$_1$-C$_4$ alkyl)), oxo (=O), thioxo (=S), or C$_1$-C$_4$ alkanoylamino (—CO—NH—(C$_1$-C$_4$ alkyl)). In some embodiments, R$^5$, R$^6$, and R$^7$ are the same or different and each is independently selected from methyl, ethyl, propyl, butyl, pentyl, and hexyl. In still other embodiments, R$^4$ is

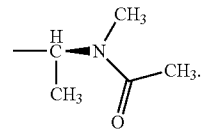

In some embodiments, m is 1, 2, 3, 4, or 5. In yet other embodiments, m is 1 or 2. In still other embodiments, Z is BSA, CSA, or HSA. In certain embodiments, Z is HSA.

In some embodiments, the compound is I-1, I-2, I-3, I-4, I-5, I-6, I-7, I-8, I-9, or I-10. In other embodiments, the compound is I-1 or I-3.

Some embodiments of the invention include compositions comprising any compound disclosed herein. In certain embodiments, the amount of the compound is from about 0.0001% (by weight total composition) to about 99%. In other embodiments, the composition comprises a lyophilized compound.

Some embodiments of the invention include pharmaceutical compositions comprising any compound disclosed herein. In still other embodiments, the amount of the compound is from about 0.0001% (by weight total composition) to about 50%. In certain embodiments, the pharmaceutical composition further comprises a formulary ingredient. In other embodiments, the pharmaceutical composition comprises a lyophilized compound.

Some embodiments of the invention include methods for providing an animal with any compound disclosed herein comprising one or more administrations of one or more compositions comprising any compound disclosed herein, wherein the compositions may be the same or different if there is more than one administration. In yet other embodiments, at least one of the one or more compositions further comprises a formulary ingredient. In other embodiments, at least one of the one or more compositions comprises any composition disclosed herein or any pharmaceutical composition disclosed herein. In certain embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In some embodiments, if there is more than one administration at least one composition used for at least one administration is different from the composition of at least one other administration. In certain embodiments, the compound of at least one of the one or more compositions is administered to the animal in an amount of from about 0.01 mg/kg animal body weight to about 500 mg/kg animal body weight. In still other embodiments, the animal is a human, a canine, or a primate.

Some embodiments of the invention include methods for treating an animal for a disease, comprising one or more administrations of one or more compositions comprising any compound disclosed herein, wherein the compositions may be the same or different if there is more than one administration. In certain embodiments, at least one of the one or more compositions further comprises a formulary ingredient. In other embodiments, at least one of the one or more compositions comprises any composition disclosed herein or any pharmaceutical composition disclosed herein. In some embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In still other embodiments, if there is more than one administration at least one composition used for at least one administration is different from the composition of at least one other administration. In certain embodiments, the compound of at least one of the one or more compositions is administered to the animal in an amount of from about 0.01 mg/kg animal body weight to about 500 mg/kg animal body weight. In still other embodiments, the animal is a human, a canine, or a primate. In yet other embodiments, the animal is in need of the treatment. In certain embodiments, the method is for treating cancer. In some embodiments, the method is for treating acute lymphoblastic leukemia, astrocytoma, basal cell carcinoma, bladder cancer, bone marrow cancer, breast cancer, chronic lymphocytic leukemia (CLL), CNS cancer, colon cancer, colorectal cancer, endometrial cancer, gastric cancer, glioblastoma, glioblastoma multiforme, glioma, gliosarcoma, head and neck cancers, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, cancers that can result in metastasis, cancers resulting from metastasis, or cancerous tumors thereof. In other embodiments, the method is for treating basal cell carcinoma, bladder cancer, bone marrow cancer, breast cancer, CNS cancer, colon cancer, colorectal cancer, endometrial cancer, gastric cancer, glioblastoma, glioblastoma multiforme, glioma, gliosarcoma, head and neck cancers, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, or cancerous tumors thereof. In yet other embodiments, the method is for treating cancerous tumors. In still other embodiments, the method is for treating breast cancer, head and neck cancer, lung cancer, non-small cell lung cancer, lymphoma, ovarian cancer, or renal cancer.

Some embodiments of the invention include methods for preparing any compound disclosed herein comprising (a) reacting Z with a disulfide to provide activated Z; (b) reacting activated Z with Formula (II) to provide the compound; and (c) optionally, recovering the compound. In certain embodiments, the Formula (II) is

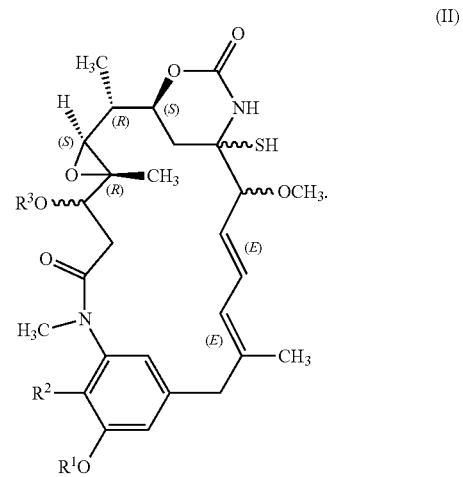

In some embodiments, the disulfide is formamidine disulfide, aldrithiol, or 5,5'-dithiobis(2-nitrobenzoic acid). In still other embodiments, the disulfide is formamidine disulfide. In other embodiments, the disulfide is at a concentration that is in mole equivalent excess of Z. In still other embodiments, prior to step (a), one or more thiol reducing agents is added to Z and, optionally, then at least some of the unreacted one or more thiol reducing agents is removed. In some embodiments, the pH of the reaction solution in step (b) is from about 1.0 to about 7.0 (e.g., from about 1.0 to about 6.0). In still other embodiments, Formula (II) is dissolved in a polar solvent prior to its addition to the activated Z. In certain embodiments, the reaction in step (b) is from about 4 hours to about 48 hours. In other embodiments, the temperature of the reaction in step (b) is from about −5° C. to about 20° C. In yet other embodiments, step (c) is not optional. In some embodiments, the method further comprises lyophilization, after step (b) or after step (c).

Other embodiments of the invention are also disclosed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
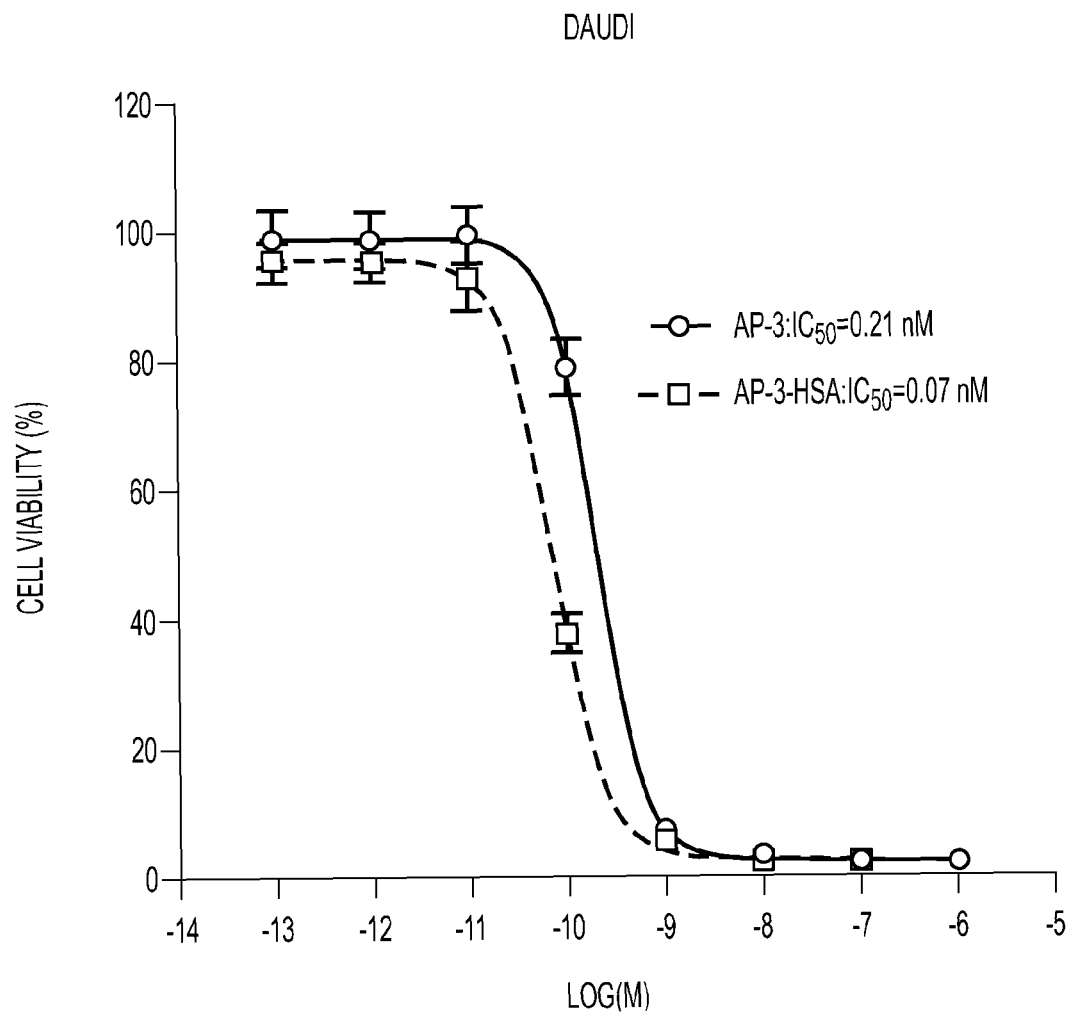
FIG. 1. Comparison of the effects AP3 and Compound I-1 on the viability of human Daudi lymphoma tumor cells after 72 h culture. The similar potencies suggest bioavailability of Compound I-1.
Figure 2:
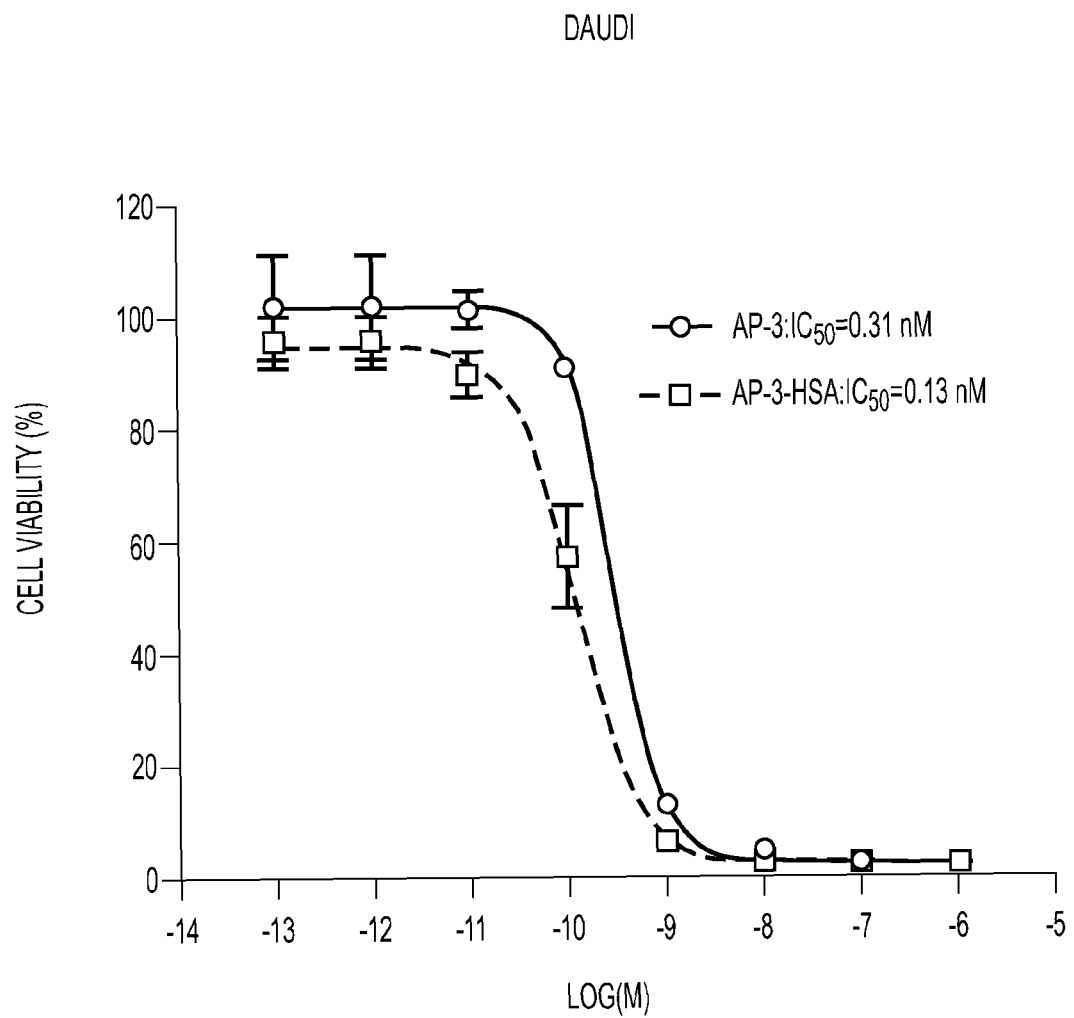
FIG. 2. Repeat experiment comparing the effects AP3 and Compound I-1 on the viability of human Daudi lymphoma tumor cells after 72 h culture. The similar potencies again suggest bioavailability of Compound I-1.
Figure 3:
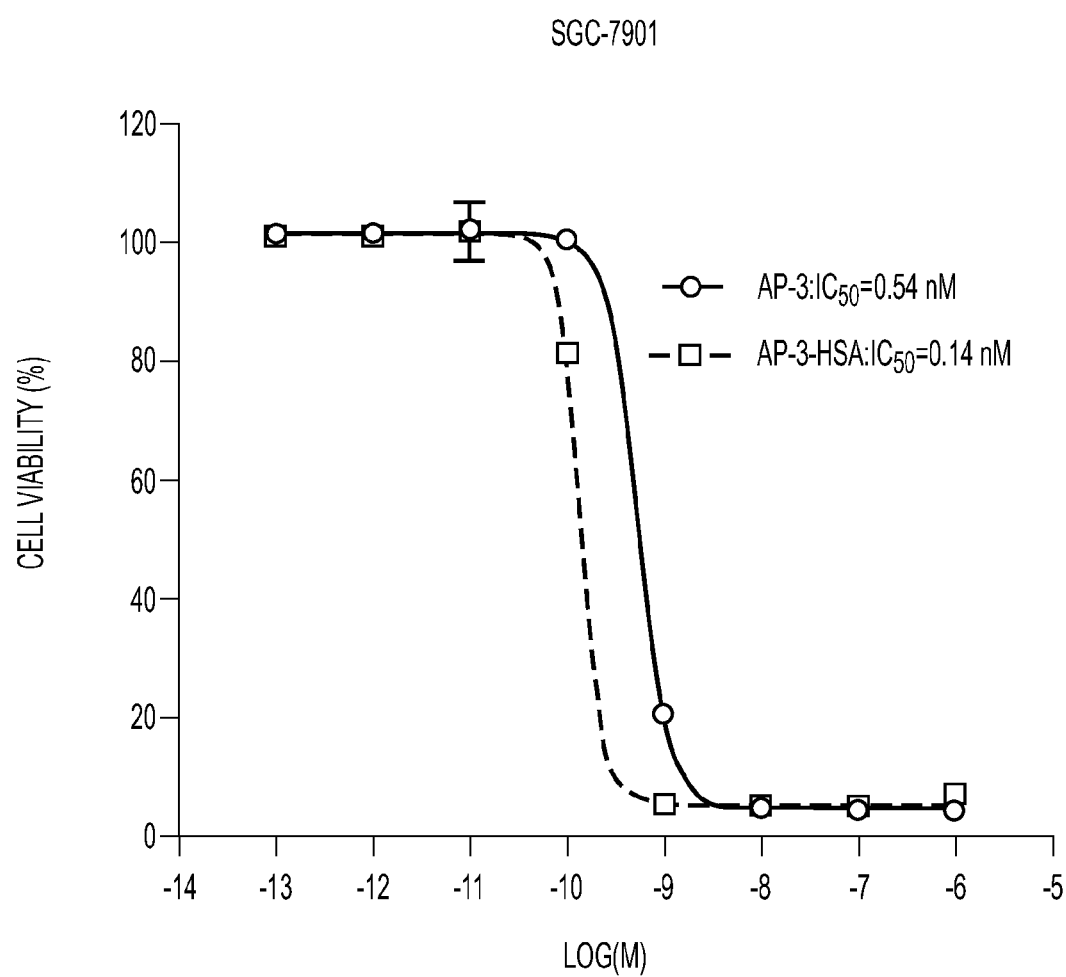
FIG. 3. Comparison of the effects AP3 and Compound I-1 on the viability of cultures of human SGC-7901 gastric tumor cells after 72 h culture. The similar potencies suggest bioavailability of Compound I-1.
Figure 4:
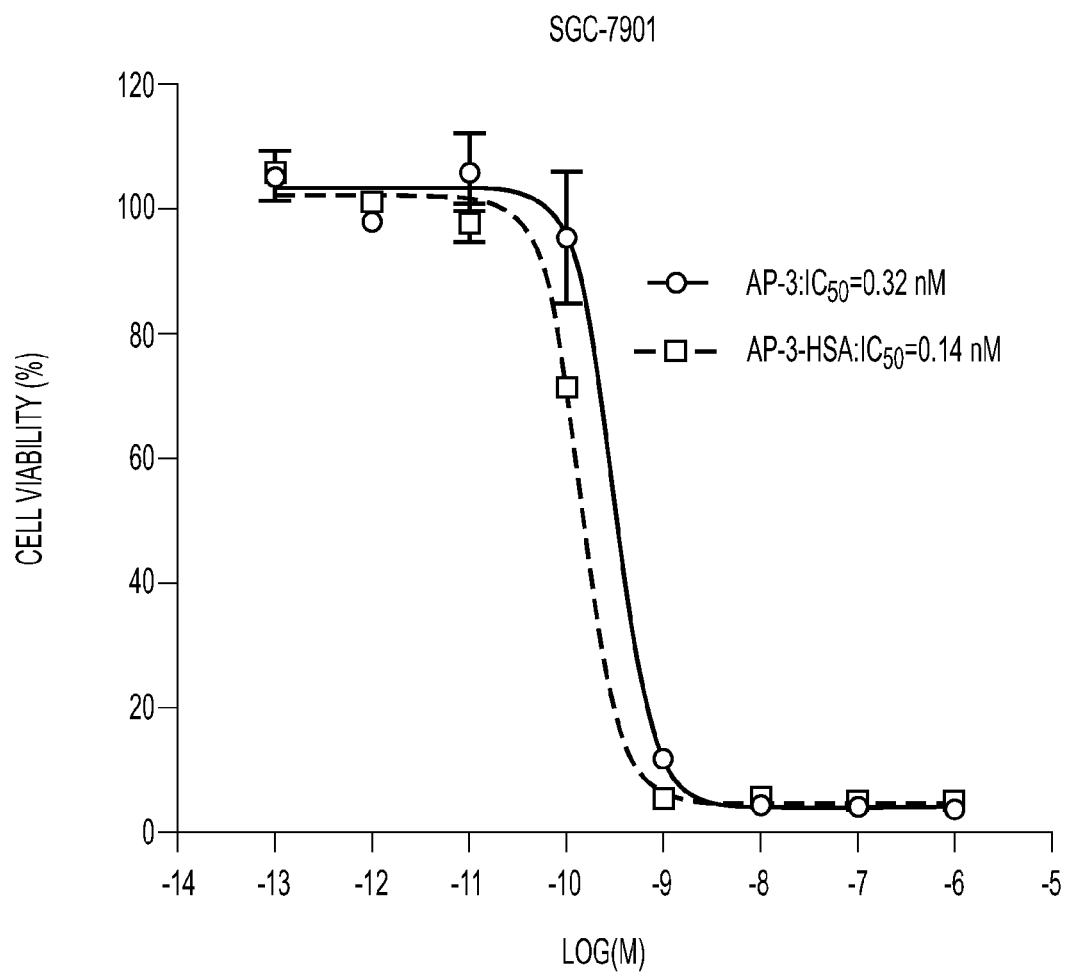
FIG. 4. Repeat experiment comparing the effects AP3 and Compound I-1 on the viability of cultures of human SGC-7901 gastric tumor cells after 72 h culture. The similar potencies again suggest bioavailability of Compound I-1.
Figure 5:
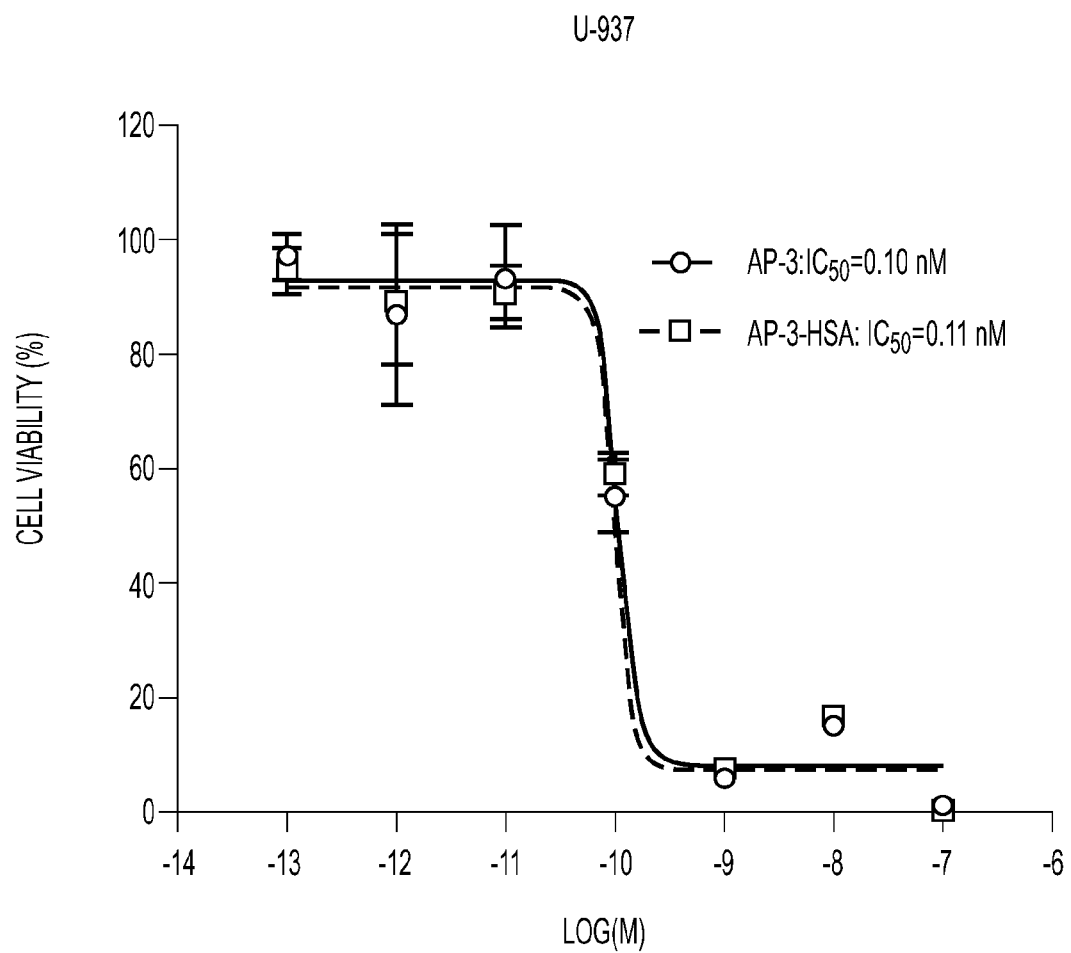
FIG. 5. Comparison of the effects AP3 and Compound I-1 on the viability of human U-937 lymphoma tumor cells after 72 h culture. The similar potencies suggest bioavailability of Compound I-1.
Figure 6:
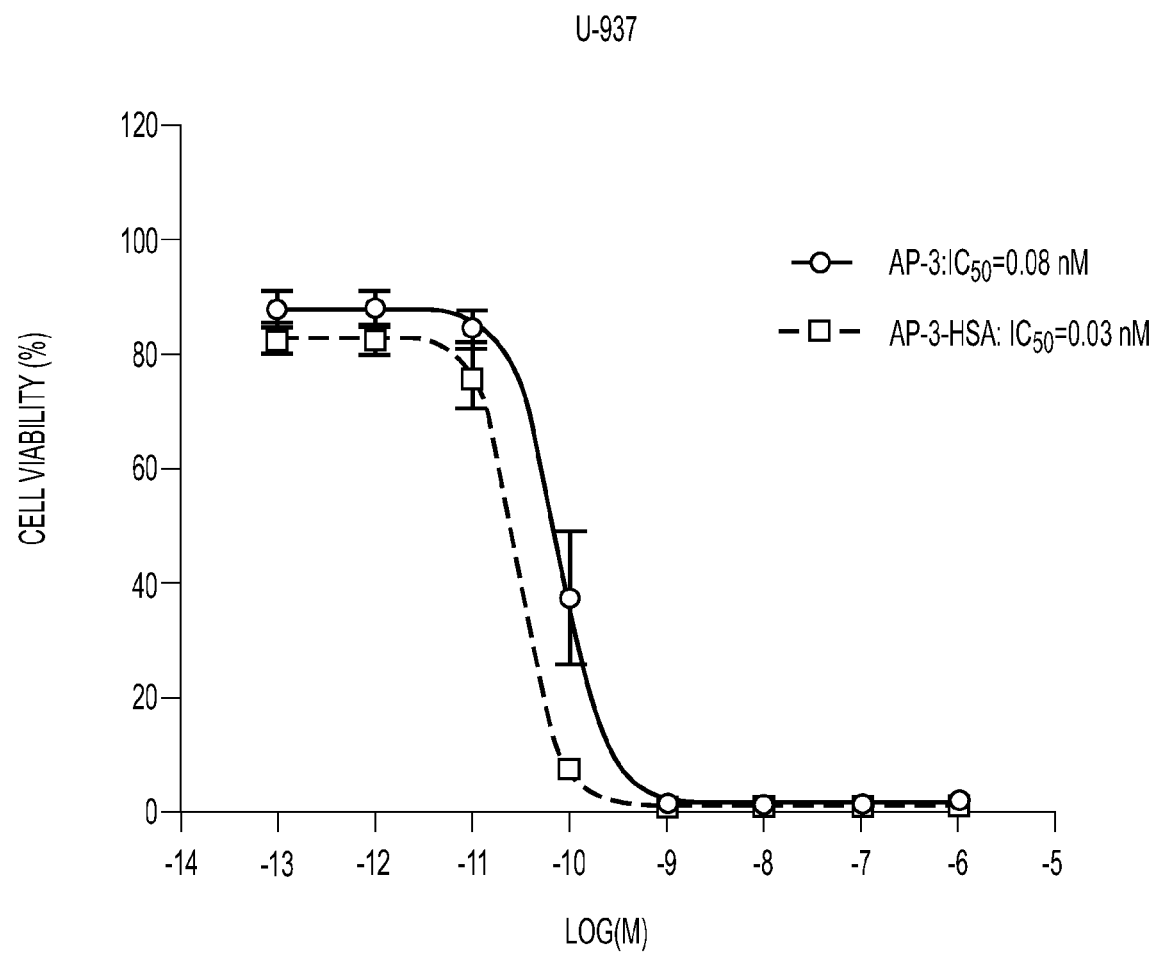
FIG. 6. Repeat experiment comparing the effects AP3 and Compound I-1 on the viability of human U-937 lymphoma tumor cells after 72 h culture. The similar potencies again suggest bioavailability of Compound I-1.
Figure 7:
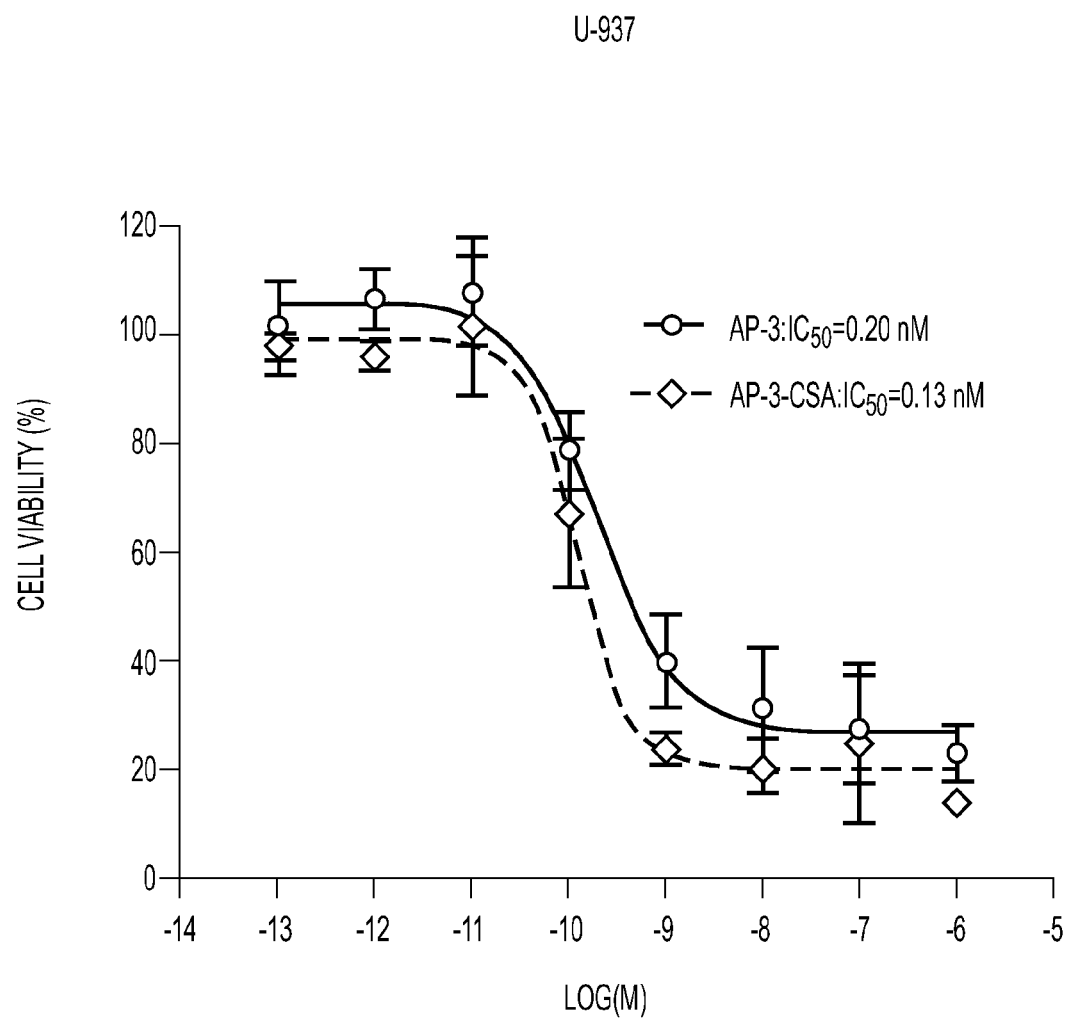
FIG. 7. Comparison of the effects AP3 and Compound I-3 on the viability of human U-937 lymphoma tumor cells after 72 h culture. The similar potencies suggest bioavailability of Compound I-3.
Figure 8:
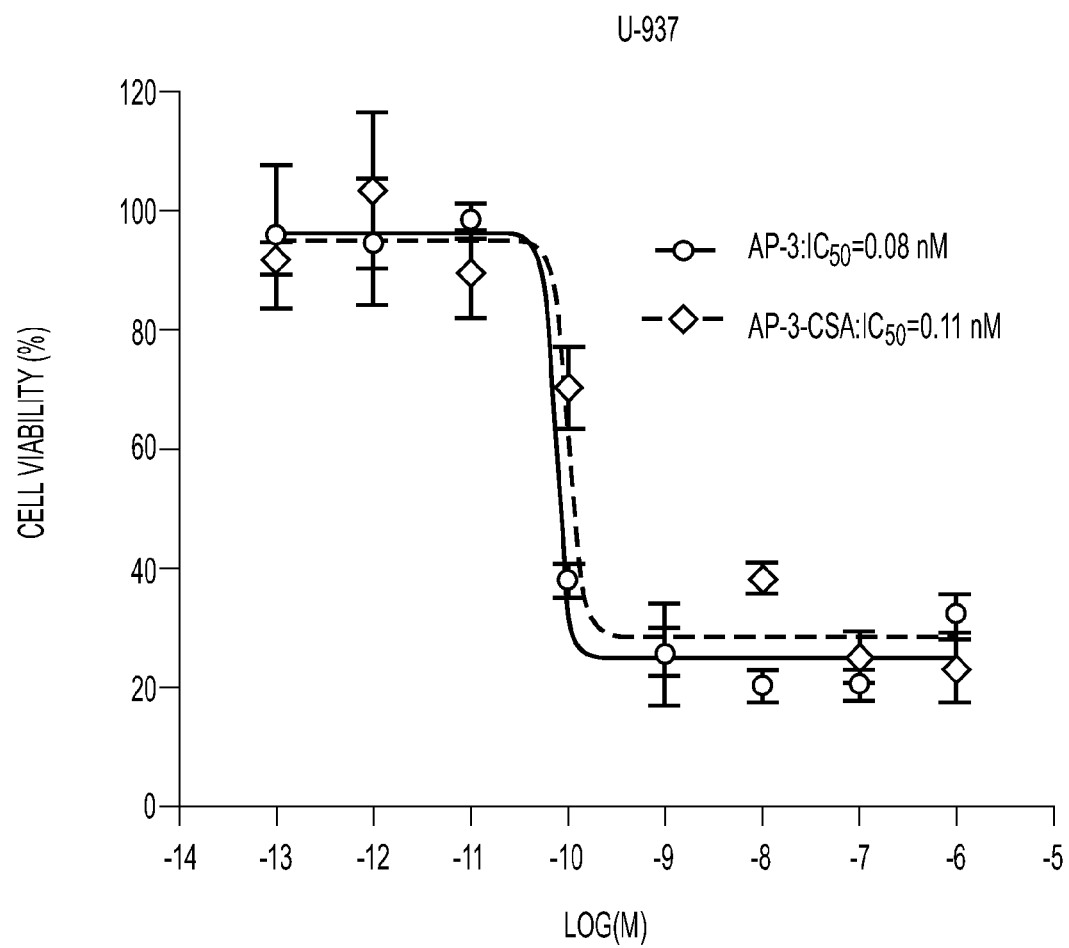
FIG. 8. Repeat experiment comparing the effects AP3 and Compound I-3 on the viability of human U-937 lymphoma tumor cells after 72 h culture. The similar potencies again suggest bioavailability of Compound I-3.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive compounds (e.g., compounds of Formula (I)). Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound. Additional embodiments of the invention are also discussed herein.

As defined herein "amino acids" include but are not limited to any naturally occurring amino acids (including but not limited to the standard 20 amino acids which are Gly, Ala, Val, Leu, Ile, Met, Pro, Phe, Trp, Ser, Thr, Asn, Gln, Tyr, Cys, Lys, Arg, His, Asp, and Glu) and unusual amino acids. As defined herein, "unusual amino acids" are amino acids that are not one of the standard 20 amino acids. Some examples of unusual amino acids are listed in Table A, but are not limited to those listed in Table A.

TABLE A

| Unusual Amino Acids | |
|---|---|
| Abbr. | Amino Acid |
| Aad | 2-Aminoadipic acid |
| BAad | 3-Aminoadipic acid |

TABLE A-continued

Unusual Amino Acids

| Abbr. | Amino Acid |
|---|---|
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Amino acids can be in the L-form, D-form, or neither (e.g., glycine). As used herein, if the amino acid three-letter or one-letter designation does not indicate, the amino acid is in the L-form, unless otherwise indicated. When not in a sequence, the form of the amino acid when designated includes a hyphen (e.g., L-Lys). When in a sequence the hyphen is removed.

As used herein (unless otherwise specified), a "fragment" of a protein or amino acid sequence includes at least 3 consecutive amino acids. For example, a fragment can include 3, 4, 5, 6, 7, 8, 9, 10, 11, 12, 13, 14, 15, 16, 17, 18, 19, 20, 25, 30, 35, 40, 45, 50, 75, 100, 125, 150, 175, 200, 250, 500, 1000, 1500, 2000, no more than 50, no more than 100, no more than 500, no more than 1000, no more than 1500, no more than 2000, at least 10, at least 15, at least 20, at least 25, at least 35, at least 40, at least 45, at least 50, at least 100, at least 150, at least 175, at least 200, at least 500, at least 1000, at least 1500, or at least 2000 consecutive amino acids of the protein or amino acid sequence. In some embodiments, a fragment can be at least 150 consecutive amino acids. In some embodiments, a fragment can be at least 175 consecutive amino acids. The length of the fragment can be appropriately changed depending on a desired property or function.

As used herein (unless otherwise specified), a "mutant" (or similar language such as mutated or mutation) of a protein or amino acid sequence includes truncations, additions, deletions, substitutions, and other alterations of the protein or amino acid sequence provided some degree of a desired property or a desired function remains. In some embodiments, the mutations can be a combination of two or more truncations, deletions, additions, substitutions, or other alterations. In some embodiments, one or more substitutions can be conservative substitutions. In some embodiments, conservative substitutions can be based on hydropathic index of Kyte and Doolittle J. Mol. Biol. 1982, Vol. 157, pp. 105-132 (e.g., substitutions of within ±2, within ±1, or within ±0.5), on hydrophilic values of U.S. Pat. No. 4,554, 101 (e.g., substitutions of within ±2, within ±1, or within ±0.5), or on the size of the amino acid (e.g., side group size). In certain embodiments, the following substitutions are considered conservative if one amino acid is substituted from another in the same group: Group 1 is Ile, Leu, Val, Ala, Gly; Group 2 is Trp, Tyr, Phe; Group 3 is Asp, Glu, Asn, Gln; Group 4 is Cys, Ser, Thr, Met; Group 5 is His, Lys, Arg. In some instances, a conservative substitution minimally disrupts (or can enhance) one or more desired properties or functions.

As used herein (unless otherwise specified), the term "alkyl" means a monovalent, straight or branched hydrocarbon chain (e.g., $C_1$-$C_{24}$). For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds (e.g., $C_2$-$C_{24}$). Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—) (e.g., $C_1$-$C_{23}$). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g., 1, 2, 3, or 4) double bonds in the chain (e.g., $C_2$-$C_{24}$). Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, or 12 member aromatic hydrocarbon group which, when unsubstituted. Examples of aryl groups include, but are not limited to, phenyl, naphthyl, tolyl, and xylyl. For a bicyclic aryl that is designated as substituted, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds), and adamantane. For a monocyclic cycloalkyl, the ring is not aromatic. For a bicyclic cycloalkyl, if one ring is aromatic, then the other is not aromatic. For a bicyclic cycloalkyl that is designated as substituted, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl, tetrazolyl, 1H-pyrazol-4-yl, 1-Me-pyrazol-4-yl, pyridin-3-yl, pyridin-4-yl, 3,5-dimethyl-isoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl that is designated as substituted, one or both rings can be substituted.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, tetrahydropyran, pyrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperidin-1-yl, piperidin-2-yl, piperidin-3-yl, or piperidin-4-yl), and morpholinyl (e.g., morpholin-1-yl, morpholin-2-yl, morpholin-3-yl, or morpholin-4-yl,). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl that is designated as substituted, one or both rings can be substituted.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

Some compounds of the invention can have one or more chiral centers and can exist in and be isolated in optically active and racemic forms, for any of the one or more chiral centers. Some compounds can exhibit polymorphism. The compounds of the present invention (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

Some embodiments of the invention include compounds of Formula (I):

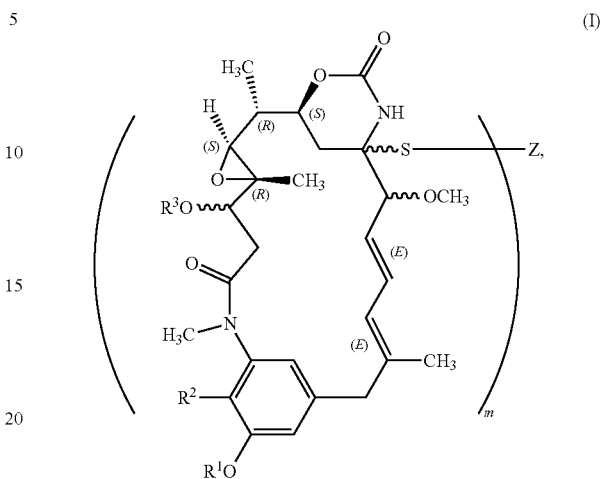

In some embodiments, the compounds of Formula (I) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g., quaternary ammonium). In yet other embodiments, simple derivatives of the compounds (e.g., ethers, esters, or amides) which have desirable retention and release characteristics but which are easily hydrolyzed by body pH, enzymes, or other suitable means, can be employed.

In some embodiments, $R^1$ can be selected from H, —$COCH_3$, carboxy (—$CO_2H$), ethynyl (—CCH), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), methyl, ethyl, perfluorinated methyl, perfluorinated ethyl, $C_1$-$C_4$ alkylsulfonyl (—S(=O)$_2$—($C_1$-$C_4$ alkyl)), and phenyl-($C_1$-$C_4$ alkyl), which —$COCH_3$, carboxy (—$CO_2H$), ethynyl (—CCH), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), methyl, ethyl, $C_1$-$C_4$ alkylsulfonyl, or phenyl-($C_1$-$C_4$ alkyl) can optionally be substituted with one or more (e.g., 0, 1, 2, 3, 4, 5, or 6) of halogen (e.g., F, Cl, Br, or I), hydroxy (—OH), methanoyl (—COH), —$COCH_3$, carboxy (—$CO_2H$), ethynyl (—CCH), cyano (—CN), sulfo (—$SO_3H$), methyl, ethyl, phenyl, perfluorinated methyl, perfluorinated ethyl, amino, $C_1$-$C_4$ alkanoylamino (—NH—CO—($C_1$-$C_4$ alkyl)), $C_1$-$C_4$ alkoxy, benzyloxy (—O—$CH_2$-phenyl), oxo (=O), $C_2$-$C_8$ alkoxycarbonyl (—CO—O—($C_2$-$C_8$ alkyl)), methylenedioxy (—O—$CH_2$—O—, with one or two attachment carbons), or $C_1$-$C_4$ alkylthio (—S—($C_1$-$C_4$ alkyl)).

In other embodiments, $R^1$ can be selected from H, —$COCH_3$, carboxy (—$CO_2H$), ethynyl (—CCH), $C_1$-$C_8$ alkyl (e.g., $C_1$, $C_2$, $C_3$, $C_4$, $C_5$, $C_6$, $C_7$, or $C_8$ alkyl), $C_2$-$C_8$ alkenyl (e.g., $C_2$, $C_3$, $C_4$, $C_5$, $C_6$, $C_7$, or $C_8$ alkenyl), $C_2$-$C_8$ alkynyl (e.g., $C_2$, $C_3$, $C_4$, $C_5$, $C_6$, $C_7$, or $C_8$ alkynyl), methyl, ethyl, perfluorinated methyl, and perfluorinated ethyl, which —COCH$_3$, carboxy (—CO$_2$H), ethynyl (—CCH), C$_1$-C$_8$ alkyl (e.g., C$_1$, C$_2$, C$_3$, C$_4$, C$_5$, C$_6$, C$_7$, or C$_8$ alkyl), C$_2$-C$_8$ alkenyl (e.g., C$_2$, C$_3$, C$_4$, C$_5$, C$_6$, C$_7$, or C$_8$ alkenyl), C$_2$-C$_8$ alkynyl (e.g., C$_2$, C$_3$, C$_4$, C$_5$, C$_6$, C$_7$, or C$_8$ alkynyl), methyl, or ethyl can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, phenyl, perfluorinated methyl, perfluorinated ethyl, amino, C$_1$-C$_4$ alkoxy, benzyloxy, oxo, or methylenedioxy. In other embodiments, R$^1$ can be selected from H, —COCH$_3$, carboxy (—CO$_2$H), ethynyl (—CCH), C$_1$-C$_4$ alkyl (e.g., C$_1$, C$_2$, C$_3$, or C$_4$ alkyl), C$_2$-C$_4$ alkenyl (e.g., C$_2$, C$_3$, or C$_4$ alkenyl), C$_2$-C$_4$ alkynyl (e.g., C$_2$, C$_3$, or C$_4$ alkynyl), methyl, ethyl, perfluorinated methyl, and perfluorinated ethyl, which —COCH$_3$, carboxy (—CO$_2$H), ethynyl (—CCH), C$_1$-C$_4$ alkyl (e.g., C$_1$, C$_2$, C$_3$, or C$_4$ alkyl), C$_2$-C$_4$ alkenyl (e.g., C$_2$, C$_3$, or C$_4$ alkenyl), C$_2$-C$_4$ alkynyl (e.g., C$_2$, C$_3$, or C$_4$ alkynyl), methyl, or ethyl can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, amino, C$_1$-C$_4$ alkoxy, or oxo. In certain embodiments, R$^1$ can be selected from H, —COCH$_3$, carboxy (—CO$_2$H), ethynyl (—CCH), methyl, ethyl, perfluorinated methyl, and perfluorinated ethyl. In certain embodiments, R$^1$ can be selected from H, methyl, and perfluorinated methyl. In some embodiments, R$^1$ can be the same as Y in U.S. Pat. No. 4,424,219 to Hashimoto et al., which is herein incorporated by reference in its entirety.

In some embodiments, R$^2$ can be selected from H, allyl, vinyl, hydroxyl, Cl, Br, F, I, thiol, amino, nitro, cyano, C$_1$-C$_4$ alkyl (e.g., C$_1$, C$_2$, C$_3$, or C$_4$ alkyl), C$_1$-C$_4$ alkylnoic (e.g., C$_1$, C$_2$, C$_3$, or C$_4$ alkylnoic), phenyl, C$_1$-C$_2$ perfluorinated alkyl, alkyl amino, oxo, carboxy, acetyl, amido, and C$_1$-C$_3$ alkoxy (e.g., C$_1$, C$_2$, or C$_3$ alkoxy). In some embodiments, R$^2$ can be H, Cl, Br, F, I, allyl, ethyl, methyl, or OH. In some embodiments, R$^2$ can be H or Cl. In some embodiments, R$^2$ can be the same as X in U.S. Pat. No. 4,424,219 to Hashimoto et al., which is herein incorporated by reference in its entirety.

In some embodiments, R$^3$ can be selected from H, C$_1$-C$_{18}$ alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, or C$_{18}$ alkyl), C$_2$-C$_{20}$ alkenyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkenyl), C$_2$-C$_{20}$ alkynyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkynyl), methyl, ethyl, perfluorinated methyl, perfluorinated ethyl, aryl (e.g., phenyl or napthyl), cycloalkyl (e.g., cyclopropyl, cyclobutyl, cyclopentyl, or cyclohexyl), and —COR$^4$, which C$_1$-C$_{18}$ alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, or C$_{18}$ alkyl), C$_2$-C$_{20}$ alkenyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkenyl), C$_2$-C$_{20}$ alkynyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkynyl), methyl, ethyl, aryl (e.g., phenyl or napthyl), or cycloalkyl (e.g., cyclopropyl, cyclobutyl, cyclopentyl, or cyclohexyl) can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, C$_1$-C$_4$ alkoxy, C$_2$-C$_4$ alkanoyl (—CO—(C$_2$-C$_4$ alkyl)), C$_2$-C$_4$ alkanoyloxy (—CO—O—(C$_2$-C$_4$ alkyl)), C$_2$-C$_4$ alkoxycarbonyl (—O—CO—(C$_2$-C$_4$ alkyl)), nitro, amino, mono(C$_1$-C$_4$ alkyl)amino, di(C$_1$-C$_4$ alkyl)amino, C$_1$-C$_4$ alkylthio (—S—(C$_1$-C$_4$ alkyl)), C$_1$-C$_4$ alkylsulfinyl (—SO—(C$_1$-C$_4$ alkyl)), C$_1$-C$_4$ alkylsulfonyl (—S(=O)$_2$—(C$_1$-C$_4$ alkyl)), oxo (=O), thioxo (=S), or C$_1$-C$_4$ alkanoylamino (—CO—NH—(C$_1$-C$_4$ alkyl)). In some embodiments, R$^3$ can be methyl, ethyl, propyl (e.g., isopropyl), butyl (e.g., isobutyl), pentyl (e.g., isopentyl), hexyl (e.g., isohexyl), heptyl (e.g., isoheptyl), octyl (e.g., isooctyl), or nonyl (e.g., isononyl). In some embodiments, R$^3$ can be isopropyl, isobutyl, isopentyl, isohexyl, isoheptyl, isooctyl, or isononyl. In other embodiments, R$^3$ can be

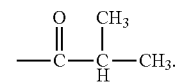

In certain embodiments, R$^3$ can be

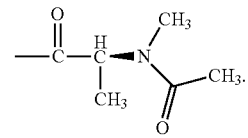

In some embodiments, R$^3$ can be the same as R in U.S. Pat. No. 4,424,219 to Hashimoto et al., which is herein incorporated by reference in its entirety.

In other embodiments, R$^4$ can be selected from C$_1$-C$_{18}$ alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, or C$_{18}$ alkyl), C$_2$-C$_{20}$ alkenyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkenyl), C$_2$-C$_{20}$ alkynyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkynyl), methyl, ethyl, perfluorinated methyl, perfluorinated ethyl, aryl (e.g., phenyl or napthyl), cycloalkyl (e.g., cyclopropyl, cyclobutyl, cyclopentyl, or cyclohexyl) and

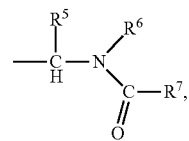

which C$_1$-C$_{18}$ alkyl (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, or C$_{18}$ alkyl), C$_2$-C$_{20}$ alkenyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkenyl), C$_2$-C$_{20}$ alkynyl (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$ alkynyl), methyl, ethyl, aryl (e.g., phenyl or napthyl), or cycloalkyl (e.g., cyclopropyl, cyclobutyl, cyclopentyl, or cyclohexyl) can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, C$_1$-C$_4$ alkoxy, C$_2$-C$_4$ alkanoyl (—CO—(C$_2$-C$_4$ alkyl)), C$_2$-C$_4$ alkanoyloxy (—CO—O—(C$_2$-C$_4$ alkyl)), C$_2$-C$_4$ alkoxycarbonyl (—O—

CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$—($C_1$-$C_4$ alkyl)), oxo (=O), thioxo (=S), or $C_1$-$C_4$ alkanoylamino (—CO—NH—($C_1$-$C_4$ alkyl)). In other embodiments, $R^4$ can be selected from $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), methyl, ethyl, perfluorinated methyl, perfluorinated ethyl, aryl (e.g., phenyl or napthyl), cycloalkyl (e.g., cyclopropyl, cyclobutyl, cyclopentyl, or cyclohexyl) and

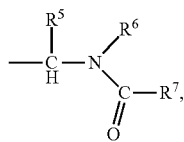

which $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), methyl, ethyl, aryl (e.g., phenyl or napthyl), or cycloalkyl (e.g., cyclopropyl, cyclobutyl, cyclopentyl, or cyclohexyl) can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$—($C_1$-$C_4$ alkyl)), oxo (=O), thioxo (=S), or $C_1$-$C_4$ alkanoylamino (—CO—NH—($C_1$-$C_4$ alkyl)). In some embodiments, $R^4$ can be methyl, ethyl, propyl (e.g., isopropyl), butyl (e.g., isobutyl), pentyl (e.g., isopentyl), hexyl (e.g., isohexyl), heptyl (e.g., isoheptyl), octyl (e.g., isooctyl), or nonyl (e.g., isononyl). In some embodiments, $R^4$ can be isopropyl, isobutyl, isopentyl, isohexyl, isoheptyl, isooctyl, or isononyl. In some embodiments, $R^4$ can be methyl, ethyl, propyl (e.g., isopropyl), butyl, pentyl, or hexyl. In some embodiments, $R^4$ can be isopropyl.

In certain embodiments, $R^4$ can be

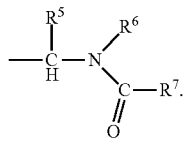

In yet other embodiments, $R^5$, $R^6$, and $R^7$ can be the same or different and each can be independently selected from $C_1$-$C_{18}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$ alkyl), $C_2$-$C_{20}$ alkenyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, Cis, $C_{19}$, or $C_{20}$ alkenyl), $C_2$-$C_{20}$ alkynyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkynyl), methyl, ethyl, perfluorinated methyl, perfluorinated ethyl, aryl (e.g., phenyl or napthyl), and cycloalkyl (e.g., cyclopropyl, cyclobutyl, cyclopentyl, or cyclohexyl), which $C_1$-$C_{18}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$ alkyl), $C_2$-$C_{20}$ alkenyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, Cis, $C_{19}$, or $C_{20}$ alkenyl), $C_2$-$C_{20}$ alkynyl (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkynyl), methyl, ethyl, aryl (e.g., phenyl or napthyl), or cycloalkyl (e.g., cyclopropyl, cyclobutyl, cyclopentyl, or cyclohexyl) can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$—($C_1$-$C_4$ alkyl)), oxo (=O), thioxo (=S), or $C_1$-$C_4$ alkanoylamino (—CO—NH—($C_1$-$C_4$ alkyl)). In still other embodiments, $R^5$, $R^6$, and $R^7$ can be the same or different and each is independently selected from $C_1$-$C_{18}$ alkyl, $C_2$-$C_{20}$ alkenyl, $C_2$-$C_{20}$ alkynyl, methyl, ethyl, perfluorinated methyl, and perfluorinated ethyl, which $C_1$-$C_{18}$ alkyl, $C_2$-$C_{20}$ alkenyl, $C_2$-$C_{20}$ alkynyl, methyl, or ethyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$—($C_1$-$C_4$ alkyl)), oxo (=O), thioxo (=S), or $C_1$-$C_4$ alkanoylamino (—CO—NH—($C_1$-$C_4$ alkyl)). In certain embodiments, $R^5$, $R^6$, and $R^7$ can be the same or different and each can be independently selected from $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), methyl, ethyl, perfluorinated methyl, or perfluorinated ethyl, which $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), methyl, or ethyl can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$—($C_1$-$C_4$ alkyl)), oxo (=O), thioxo (=S), or $C_1$-$C_4$ alkanoylamino (—CO—NH—($C_1$-$C_4$ alkyl)). In some embodiments, $R^5$, $R^6$, and $R^7$ can be the same or different and each can be independently selected from methyl, ethyl, propyl (e.g., isopropyl), butyl (e.g., isobutyl), pentyl (e.g., isopentyl), hexyl (e.g., isohexyl), heptyl (e.g., isoheptyl), octyl (e.g., isooctyl), and nonyl (e.g., isononyl). In some embodiments, $R^5$, $R^6$, and $R^7$ can be the same or different and each can be independently selected from isopropyl, isobutyl, isopentyl, isohexyl, isoheptyl, isooctyl, and isononyl. In some embodiments, $R^5$, $R^6$, and $R^7$ can be the same or different and each can be independently selected from methyl, ethyl, propyl (e.g., isopropyl), butyl, pentyl, and hexyl. In some embodiments, $R^5$, $R^6$, and $R^7$ can be the same and are methyl.

In other embodiments, $R^4$ can be

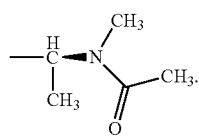

In some embodiments, $R^4$, $R^5$, $R^6$, and $R^7$ can be the same as $R^1$, $R^2$, $R^3$, and $R^4$, respectively, in U.S. Pat. No. 4,424,219 to Hashimoto et al., which is herein incorporated by reference in its entirety.

In some embodiments, m can be 1, 2, 3, 4, 5, 6, 7, 8, 9, or 10. In some embodiments, m can be 1, 2, 3, 4, or 5. In certain embodiments, m is 1 or m is 2. In some embodiments, a solution comprising Formula (I) can have a mixture of formulas that have different values of m, resulting in a solution which can yield an average m value. In some examples, the solution averaged m-value can be, but is not limited to any rational number from 1 to 10, such as about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.5, about 4, about 4.5, about 5, about 5.5, about 6, about 6.5, about 7, about 7.5, about 8, about 8.5, about 9, about 9.5, or about 10.

In some embodiments, the Z can be, but is not limited to, an albumin, human serum albumin (HSA), bovine serum albumin (BSA), canine serum albumin (CSA), feline serum albumin (FSA), equine serum albumin (ESA), Domain I of HSA, Domain II of HSA, Domain III of HSA, an engineered albumin (e.g., Veltis® from Novozymes), mutants thereof, or fragments thereof (including fragments of mutants). In other embodiments, the Z can be BSA, CSA, or HSA. In other embodiments, the Z can be BSA or HSA. In other embodiments, the Z can be CSA or HSA. In other embodiments, the Z can be HSA.

In other embodiments, Z stabilizes the compound. Stabilizing the compound can include, for example, maintaining or modulating (e.g., increasing or decreasing) any suitable desired property or function of the compound, including but not limited to water solubility (e.g., increasing), half-life in the blood (e.g., increasing), half-life in the body prior to reaching a target (e.g., increasing), stability in circulation prior to reaching a target (e.g., increasing), prevention of or decreased absorption by the kidney, or prevention of or decreased absorption by the brain.

In certain embodiments, Z is connected to the

···〰S— in the inventive compounds (e.g., Formula (I)) via a free thiol on Z. In other embodiments, Z is HSA and Z is connected to the

···〰S— in the inventive compounds (e.g., Formula (I)) via cys-34. In other embodiments, Z is CSA and Z is connected to the

···〰S— in the inventive compounds (e.g., Formula (I)) via cys-34. In other embodiments, Z is BSA and Z is connected to the

···〰S— in the inventive compounds (e.g., Formula (I)) via cys-34. In yet other embodiments, Z (e.g., HSA or domain I of HSA) is connected to the

···〰S— in the inventive compounds (e.g., Formula (I)) via a free thiol on Z that has been activated (e.g., using any suitable activating compound, such as but not limited to formamidine disulfide, as described herein). In still other embodiments, Z (e.g., canine, feline, equine, or bovine albumins) is connected to the

···〰S— in the inventive compounds (e.g., Formula (I)) via a free thiol on Z that has been activated (e.g., using any suitable activating compound, such as but not limited to formamidine disulfide, as described herein) after Z was reacted with a reducing compound (e.g., using any suitable reducing compound, such as but no limited to mercaptoethanol or dithiothreitol)

In some embodiments, the compounds of Formulas (I) can be selected from those specified in Table 1.

| Formula # (other identifiers) | Structure |
|---|---|
| I-1 (AP3-HSA; AP-3-HSA) | 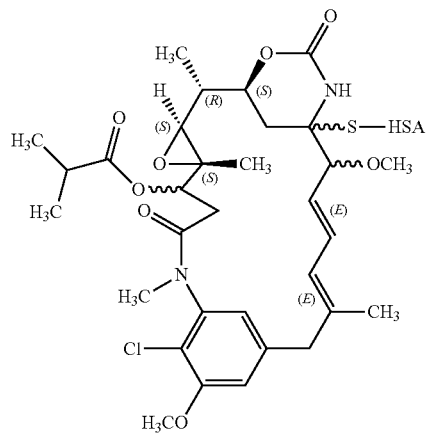 (the Human Serum Albumin (HSA) is attached via its cys-34 thiol) |
| I-2 (AP3-BSA) | 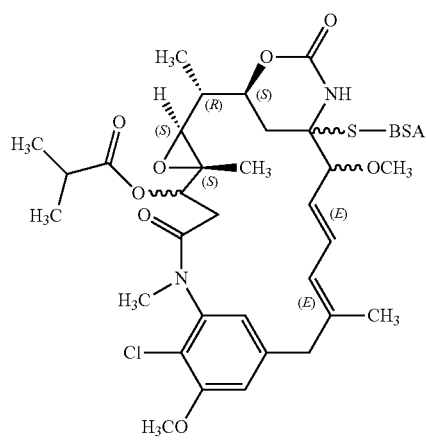 (the Bovine Serum Albumin (BSA) is attached via its cys-34 thiol) |
| I-3 (AP3-CSA) | 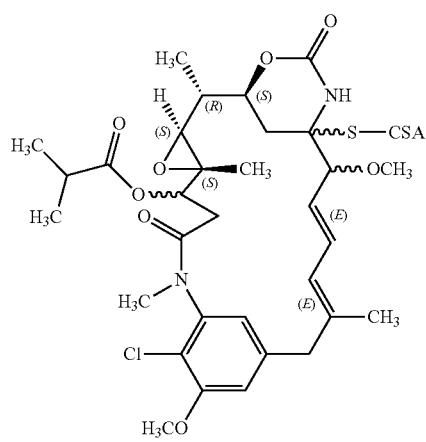 (the Canine Serum Albumin (CSA) is attached via its cys-34 thiol) |
| I-4 | 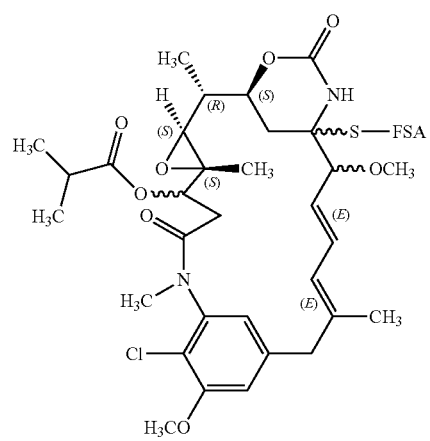 (the Feline Serum Albumin (FSA) is attached via its cys-34 thiol) |
| I-5 | 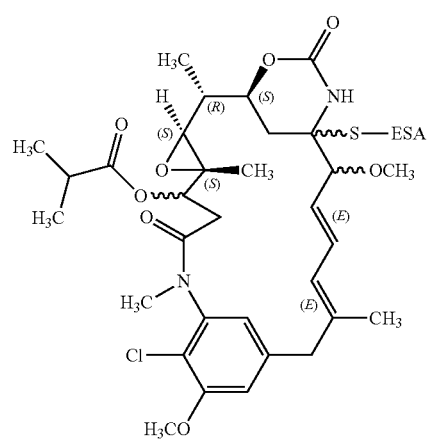 (the Equine Serum Albumin (ESA) is attached via its cys-34 thiol) |
| I-6 | 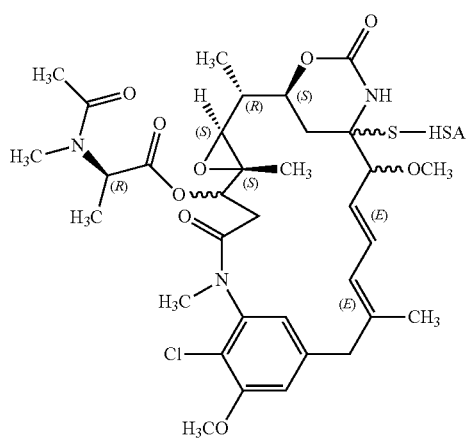 (the Human Serum Albumin (HSA) is attached via its cys-34 thiol) |

| Formula # (other identifiers) | Structure |
|---|---|
| I-7 | (structure diagram; the Bovine Serum Albumin (BSA) is attached via its cys-34 thiol) |
| I-8 | (structure diagram; the Canine Serum Albumin (CSA) is attached via its cys-34 thiol) |
| I-9 | (structure diagram, S—FSA) |
| I-10 | (structure diagram, S—ESA) |

In some embodiments, the compound of the invention can be I-1, I-2, I-3, I-4, I-5, I-6, I-7, I-8, I-9, or I-10. In some embodiments, the compound of the invention can be I-1, I-2, I-3, I-4, or I-5. In other embodiments, the compound of the invention can be I-1, I-2, I-3, I-6, or I-7. In still other embodiments, the compound of the invention can be I-1 or I-3. In still other embodiments, the compound of the invention can be I-1.

Compositions Including Pharmaceutical Compositions

One or more compounds of the invention (e.g., Formula (I)) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

One or more compounds of the invention (e.g., Formula (I)) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising compounds of the invention (e.g., Formula (I)). In certain embodiments, the composition is a pharmaceutical composition, such as compositions that are suitable for administration to animals (e.g., mammals, primates, monkeys, humans, canine, feline, equine, bovine, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

In some embodiments, compounds of the invention (e.g., Formula (I)) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for a compound of the invention (e.g., Formula (I)), for the dosage of a compound of the invention (e.g., Formula (I)), for the timing of release of a compound of the invention (e.g., Formula (I)), for the disease, for the disease state, for the diseased organ, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release a compound of the invention (e.g., one or more compounds of Formula (I)) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating a compound of the invention (e.g., Formula (I)) (or control release formulation) into food, food stuffs, feed, or drink.

Yet other formulations (e.g., formulations of a pharmaceutical composition) can, in certain embodiments, include lyophilized compounds of the invention (e.g., Formula (I)) which can comprise (in some instances) any suitable substance to stabilize one or more of the inventive compounds, such as but not limited to one or more simple carbohydrates (e.g., sucrose, mannitol, trehalose, or a combination thereof).

Other embodiments of the invention can include methods of administering or treating an animal (e.g., human or canine), which can involve treatment with an amount of at least one compound of the invention (e.g., Formula (I)) that is effective to treat a cancer that the animal has, or is suspected of having, or is susceptible to, or to bring about a desired physiological effect. In some embodiments, the composition or pharmaceutical composition comprises at least one compound of the invention (e.g., Formula (I)) which can be administered to an animal (e.g., mammals, primates, monkeys, or humans) in an amount of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.01 to about 15 mg/kg body weight, about 0.1 to about 10 mg/kg body weight, about 0.5 to about 7 mg/kg body weight, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention can be administered in combination with one or more other therapeutic agents for cancer.

In some embodiments, the compositions can include a dose (e.g., unit dose) of one or more compounds of the invention (e.g., Formula (I)) in combination with a pharmaceutically acceptable carrier and, in addition, can include other medicinal agents, pharmaceutical agents, carriers, adjuvants, diluents, excipients, or combinations thereof. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Parenteral administration, if used, is generally characterized by injection. Sterile injectables can be prepared in conventional forms, either as liquid solutions or suspensions, solid forms suitable for solution or suspension in liquid prior to injection, or as emulsions.

Methods for Administering and for Treatment

The compounds of the invention (e.g., Formula (I)) can be administered to animals by any number of suitable administration routes or formulations. The compounds of the invention (e.g., Formula (I)) can also be used to treat animals for a variety of diseases. Animals include but are not limited to mammals, primates, monkeys (e.g., macaque, rhesus macaque, or pig tail macaque), humans, canine, feline, equine, bovine, porcine, avian (e.g., chicken), mice, rabbits, and rats. As used herein, the term "subject" refers to both human and animal subjects.

The route of administration of the compounds of the invention (e.g., Formula (I)) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend, for example, on the identity of the compound of the invention (e.g., Formula (I)) (e.g., the physical and chemical properties of compound of the invention (e.g., Formula (I))) as well as the age and weight of the animal, the particular disease (e.g., cancer), and the severity of the disease (e.g., stage of the cancer). Of course, combinations of administration routes can be administered, as desired.

Some embodiments of the invention include methods for providing a subject with a composition comprising a compound of the invention (e.g., Formula (I)) described herein (e.g., a pharmaceutical composition) which comprises one or more administrations of one or more such compositions; the compositions may be the same or different if there is more than one administration and the routes of administration may be the same or different if there is more than one administration.

Some embodiments of the invention include methods for treating a subject with a composition comprising a compound of the invention (e.g., Formula (I)) described herein (e.g., a pharmaceutical composition) which comprises one or more administrations of one or more such compositions; the compositions may be the same or different if there is more than one administration and the routes of administration may be the same or different if there is more than one administration.

Animals that can be treated include but are not limited to mammals, primates, monkeys (e.g., macaque, rhesus macaque, pig tail macaque), humans, canine, feline, equine, porcine, avian (e.g., chicken), bovine, mice, rabbits, and rats. As used herein, the term "subject" refers to both human and animal subjects. A subject susceptible to a disease (e.g., cancer) can be a human subject or an animal subject. In some instances, the animal (e.g., human or canine) is in need of the treatment for cancer.

Diseases that can be treated in an animal (e.g., mammals, porcine, canine, avian (e.g., chicken), bovine, feline, primates, rodents, monkeys, rabbits, mice, rats, and humans) using a compound of the invention (e.g., Formula (I) or (I-1)) include, but are not limited to cancers.

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I) or (I-1)) include, but are not limited to, acute lymphoblastic leukemia, astrocytoma, basal cell carcinoma, bladder cancer, bone marrow cancer, breast cancer, chronic lymphocytic leukemia (CLL), CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, head and neck cancers, hepatocellular carcinoma, kidney cancer (e.g., renal cancer), leukemia, liver cancer, lung cancer (e.g., non-small cell lung cancer), lymphoma, melanoma (e.g., cutaneous malignant melanoma or melanoma tumorigenesis), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In some embodiments, cancers that can be treated include, but are not limited to, basal cell carcinoma, bladder cancer, bone marrow cancer, breast cancer, CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, head and neck cancers, hepatocellular carcinoma, kidney cancer (e.g., renal cancer), leukemia, liver cancer, lung cancer (e.g., non-small cell lung cancer), lymphoma, melanoma (e.g., cutaneous malignant melanoma or melanoma tumorigenesis), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cancer, renal cell carcinoma, rhabdomyosarcoma, squamous cell carcinoma (e.g., head and neck squamous cell carcinoma), stomach cancer, thyroid cancer, uterine cancer, or cancerous tumors thereof. In some embodiments, cancers that can be treated include, but are not limited to, leukemia, lung cancer (e.g., non-small cell lung cancer), head and neck cancers, colorectal cancer (e.g., colon cancer or rectal cancer), CNS cancer (e.g., glioblastoma, glioblastoma multiforme, gliosarcoma, or astrocytoma), lymphoma, melanoma (e.g., cutaneous malignant melanoma or melanoma tumorigenesis), ovarian cancer, renal cancer, kidney cancer, prostate cancer, breast cancer, or cancerous tumors thereof. In some embodiments, cancers that can be treated include, but are not limited to, breast cancer, head and neck cancer, lung cancer (e.g., non-small cell lung cancer), lymphoma, ovarian cancer, renal cancer, or cancerous tumors thereof. In some embodiments, cancers that can be treated include, but are not limited to, breast cancer, head and neck cancer, lung cancer (e.g., non-small cell lung cancer), lymphoma, ovarian cancer, or renal cancer. In some embodiments, cancers that can be treated include, but are not limited to, cancerous tumors. Animals that can be treated include but are not limited to mammals, rodents, primates, monkeys (e.g., macaque, rhesus macaque, pig tail macaque), humans, canine, feline, porcine, equine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In some embodiments, cancers that can be treated in an animal (e.g., mammals, porcine, canine, equine, avian (e.g., chicken), bovine, feline, primates, rodents, monkeys, rabbits, mice, rats, and humans) using a compound of the invention (e.g., Formula (I) or (I-1)) include, but are not limited to cancers that are affected (e.g., decreased tumor size) by tubulin inhibitors.

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating cancer (e.g., breast cancer, lung cancer (e.g., non-small cell lung cancer), lymphoma, ovarian cancer, renal cancer, or cancerous tumors thereof), treating can include but is not limited to prophylactic treatment and therapeutic treatment. As such, treatment can include, but is not limited to: preventing cancer (e.g., breast cancer, lung cancer (e.g., non-small cell lung cancer), lymphoma, ovarian cancer, renal cancer, or cancerous tumors thereof); reducing the risk of cancer (e.g., breast cancer, lung cancer (e.g., non-small cell lung cancer), lymphoma, ovarian cancer, renal cancer, or cancerous tumors thereof); ameliorating or relieving symptoms of cancer (e.g., breast cancer, lung cancer (e.g., non-small cell lung cancer), lymphoma, ovarian cancer, renal cancer, or cancerous tumors thereof); eliciting a bodily response against cancer (e.g., breast cancer, lung cancer (e.g., non-small cell lung cancer), lymphoma, ovarian cancer, renal cancer, or cancerous tumors thereof); inhibiting the development or progression of cancer (e.g., breast cancer, lung cancer (e.g., non-small cell lung cancer), lymphoma, ovarian cancer, renal cancer, or cancerous tumors thereof); inhibiting or preventing the onset of symptoms associated with cancer (e.g., breast cancer, lung cancer (e.g., non-small cell lung cancer), lymphoma, ovarian cancer, renal cancer, or cancerous tumors thereof); reducing the severity of cancer (e.g., breast cancer, lung cancer (e.g., non-small cell lung cancer), lymphoma, ovarian cancer, renal cancer, or cancerous tumors thereof); causing a regression of cancer (e.g., breast cancer, lung cancer (e.g., non-small cell lung cancer), lymphoma, ovarian cancer, renal cancer, or cancerous tumors thereof) or one or more of the symptoms associated with cancer (e.g., a decrease in tumor size); causing remission of cancer (e.g., breast cancer, lung cancer (e.g., non-small cell lung cancer), lymphoma, ovarian cancer, renal cancer, or cancerous tumors thereof); or preventing relapse of cancer (e.g., breast cancer, lung cancer (e.g., non-small cell lung cancer), lymphoma, ovarian cancer, renal cancer, or cancerous tumors thereof). In some embodiments, treating does not include prophylactic treatment of cancer (e.g., preventing or ameliorating future cancer).

Treatment of an animal can occur using any suitable administration method (such as those disclosed herein) and using any suitable amount of a compound of the invention (e.g., Formula (I) or (I-1)). In some embodiments, methods of treatment comprise treating an animal for cancer (e.g., breast cancer, lung cancer (e.g., non-small cell lung cancer), lymphoma, ovarian cancer, renal cancer, or cancerous tumors thereof). Some embodiments of the invention include a method for treating a subject (e.g., an animal such as a human or primate) with a composition comprising a compound of the invention (e.g., Formula (I) or (I-1)) (e.g., a pharmaceutical composition) which comprises one or more administrations of one or more such compositions; the compositions may be the same or different if there is more than one administration.

In some embodiments, the method of treatment includes administering an effective amount of a composition comprising a compound of the invention (e.g., Formula (I) or (I-1)). As used herein, the term "effective amount" refers to a dosage or a series of dosages sufficient to affect treatment (e.g., to treat cancer, such as but not limited to breast cancer, lung cancer (e.g., non-small cell lung cancer), lymphoma, ovarian cancer, renal cancer, or cancerous tumors thereof) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of the invention (e.g., Formula (I) or (I-1)) (which can be administered to an animal such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg human body weight or about 6.5 mg/kg human body weight. In some instances, an effective amount of at least one compound of the invention (e.g., Formula (I) or (I-1)) (which can be administered to an animal such as mammals, rodents, mice, rabbits, feline, equine, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of at least one compound of the invention (e.g., Formula (I) or (I-1)) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 20 mg/kg human body weight or about 100 mg/kg human body weight. In some instances, an effective amount of at least one compound of the invention (e.g., Formula (I) or (I-1)) (which can be administered to an animal such as mammals, rodents, mice, rabbits, feline, equine, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., decreasing tumor size). A therapeutically effective amount can be administered in one or more administrations. For some purposes of this invention, a therapeutically effective amount is an amount appropriate to treat an indication (e.g., to treat cancer). By treating an indication is meant achieving any desirable effect, such as one or more of palliate, ameliorate, stabilize, reverse, slow, or delay disease (e.g., cancer) progression, increase the quality of life, or to prolong life. Such achievement can be measured by any suitable method, such as but not limited to measurement of tumor size.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the administration of at least one compound of the invention (e.g., Formula (I) or (I-1)) is an adjuvant cancer therapy or part of an adjuvant cancer therapy. Adjuvant treatments include treatments by the mechanisms disclosed herein and of cancers as disclosed herein, including, but not limited to tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In still other embodiments, a compound of the invention (e.g., Formula (I) or (I-1)) can be used as adjuvant with other chemotherapeutic agents. The use of a compound of the invention (e.g., Formula (I) or (I-1)) can, in some instances, reduce the duration of the dose of both drugs and drug combinations reducing the side effects.

In some embodiments, the treatments disclosed herein can include use of other drugs (e.g., antibiotics) or therapies for treating disease. For example, antibiotics can be used to treat infections and can be combined with a compound of the invention to treat disease (e.g., infections associated with cancer). In other embodiments, intravenous immunoglobulin (IVIG) therapy can be used as part of the treatment regime (e.g., in addition to administration of the compound(s) of the invention).

Method for Preparing Compounds of the Invention (e.g., Formula (I))

Some embodiments of the present invention include methods for the preparation of compounds of the invention (e.g., Formula (I)). In certain embodiments, a compound of the invention (e.g., Formula (I)) can be prepared comprising the step of reacting Z (as described here, such as HSA or BSA) with a disulfide (e.g., formamidine disulfide) to result in an activated Z. In other embodiments, the disulfide can be any suitable disulfide for the reaction (e.g., a disulfide suitable for linking Z to Formula (II) with a disulfide bond), including but not limited to formamidine disulfide, aldrithiol, 5,5'-dithiobis(2-nitrobenzoic acid), the disulfides disclosed in SADOWSKY et al. (2017) "Development of Efficient Chemistry to Generate Site-Specific Disulfide-Linked Protein- and Peptide-Payload Conjugates: Application to THIOMAB Antibody-Drug Conjugates" Bioconjugate Chem., Vol. 28, pp. 2086-2098 (which is incorporated herein in its entirety), and the disulfides disclosed in ANDREU et al. (1994) "Formation of Disulfide Bonds in Synthetic Peptides and Proteins" from Methods in Molecular Biology, Vol. 35: Peptide Synthesis Protocols, Edited by: M. W. Pennington and B. M. Dunn, Humana Press Inc., Totowa, NJ (which is incorporated herein in its entirety). In still other embodiments, the disulfide is formamidine disulfide or 5,5'-dithiobis(2-nitrobenzoic acid). In yet other embodiments, the disulfide is formamidine disulfide. In certain embodiments, the pH of the reaction solution can be from about 1.0 to about 6.0, from about 2.0 to about 5.0, from about 3.0 to about 4.0, about 1.0, about 1.5, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.5, or about 6.0. In other embodiments, the reaction solution comprises a buffer system (e.g., comprising 0.1 M sodium acetate or comprising 0.1 M sodium acetate with 150 mM sodium chloride). In some embodiments, the disulfide (e.g., formamidine disulfide) is at a concentration that is a mole equivalent excess of Z; for example, the disulfide (e.g., formamidine disulfide) can be at a concentration that is in mole equivalent excess of Z of from about 1.0 to about 20.0, from about 5.0 to about 15.0, from about 8.0 to about 12.0, about 1.0, about 1.05, about 1.1, about 1.15, about 1.2, about 1.25, about 1.3, about 1.35, about 1.4, about 1.45, about 1.5, about 1.6, about 1.7, about 1.8, about 1.9, about 2.0, about 3.0, about 4.0, about 5.0, about 6.0, about 7.0, about 8.0, about 9.0, about 10.0, about 11.0, about 12.0, about 13.0, about 14.0, about 15.0, about 16.0, about 17.0, about 18.0, about 19.0, or about 20.0. In some embodiments, after this reaction step (e.g., after the reaction has started, when the reaction is partially complete (e.g., >50% complete), when the reaction is nearly complete (e.g., >80% complete), or when the reaction is complete (e.g., >95% complete)), some or all of the unreacted disulfide (e.g., formamidine disulfide) can be removed; for example, this removal can occur using any suitable method including but not limited to HPLC (e.g., reverse phase), LC, precipitation, centrifugation, column chromatography (e.g., size exclusion chromatography, Sephadex G-25 size exclusion chromatography or ion exchange chromatography), use of silica gel, or combinations thereof. In some embodiments, the activated Z comprises an S-substituted thiosothiourea structure, as a result of the reaction.

In some embodiments, prior to reacting Z (e.g., BSA, canine albumin, or non-human albumin) with disulfide (e.g., formamidine disulfide), it can be optional to add one or more thiol reducing agents to Z (e.g., any suitable thiol reducing agent, such as but not limited to mercaptoethanol or dithiothreitol) at any suitable concentration (e.g., about 1 mM, about 5 mM, about 10 mM, about 15 mM, or about 20 mM). It is further optional to then remove some or all of the unreacted thiol reducing agents; for example, this removal can occur using any suitable method including but not limited to HPLC (e.g., reverse phase), LC, precipitation, centrifugation, column chromatography (e.g., size exclusion chromatography, Sephadex G-25 size exclusion chromatography or ion exchange chromatography), use of silica gel, or combinations thereof.

Formula (II) is provided R

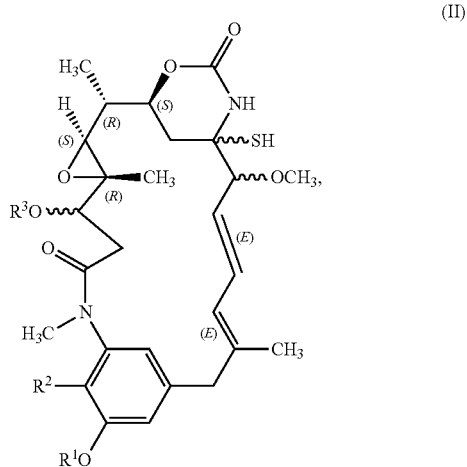

(II)

where $R^1$, $R^2$, and $R^3$ are the same as those disclosed herein. Formula (II) can be purchased or can be synthesized using any suitable method, including but not limited to those disclosed herein and those disclosed in U.S. Pat. No. 4,424,219 to Hashimoto et al., which is herein incorporated by reference in its entirety. In some embodiments, Formula (II) can be synthesized by contacting a starting compound (e.g., any compound of formula (II) where the —SH is replace by an —OH, such as ansamitocin P3 (AP3) or maytansine) with a solution comprising $P_2S_5$ (e.g., a solution comprising $P_2S_5$ and pyridine) for any suitable period of time (e.g., from 0.25 hours to 8 hours, 0.25 hours, 0.5 hours, 1 hours, 2 hours, 3 hours, 4, hours, 5 hours 6 hours, 7 hours or 8 hours) at any suitable temperature or set of temperatures (e.g., from 15° C. to 100° C., from 15° C. to 80° C., room temperature, 15° C., 20° C., 25° C., 30° C., 35° C., 40° C., 45° C., 50° C., 55° C., 60° C., 65° C., 70° C., 75° C., 80° C., 85° C., 90° C., 95° C., or 100° C.; 30 minutes at room temperature and then 3 hours at 65° C.). In other embodiments, Formula (II) can be synthesized by contacting a solution comprising starting compound (e.g., AP3 or maytansine) (e.g., a solution comprising the starting compound dissolved in methylene chloride) with $H_2S$ or a solution comprising $H_2S$ (e.g., by bubbling $H_2S$ gas into the starting compound solution); a solution comprising Trifluoroacetic acid (TFA) (e.g., TFA in methylene chloride) can, in certain embodiments, be contact with the starting compound (e.g., AP3 or maytansine)/$H_2S$ solution at any suitable temperature (e.g., from 15° C. to 100° C., from 15° C. to 80° C., room temperature, 15° C., 20° C., 25° C., 30° C., 35° C., 40° C., 45° C., 50° C., 55° C., 60° C., 65° C., 70° C., 75° C., 80° C., 85° C., 90° C., 95° C., or 100° C.) for any suitable period of time (e.g., from 0.25 hours to 72 hours, 0.25 hours, 0.5 hours, 1 hours, 2 hours, 3 hours, 4, hours, 5 hours, 6 hours, 7 hours, 8 hours, 9 hours, 10 hours, 11 hours, 12 hours, 13 hours, 14 hours, 15 hours, 16 hours, 18 hours, 20 hours, 24 hours, 32 hours, 40 hours, 48 hours, 56 hours, 64 hours, or 72 hours). In certain embodiments, recovery of Formula (II) is optional. In other embodiments, recovery of Formula (II) can optionally occur using any suitable method including but not limited to HPLC (e.g., reverse phase), LC, precipitation, centrifugation, column chromatography (e.g., size exclusion chromatography or ion exchange chromatography), use of silica gel, or combinations thereof. In some embodiments, recovery of Formula (II) can be accomplished using a HPLC with a linear solvent gradient (e.g., as disclosed herein). In some embodiments of the synthesis of Formula (II), water can be optionally removed in the starting compound (e.g., AP3 or maytansine) powder (e.g., by drying at 40° C. under vacuum) and/or $P_2S_5$ (e.g., by drying at 40° C. under vacuum).

In other embodiments (e.g., of the synthesis of Formula (II)), refluxing pyridine with calcium hydride and distilling (e.g., before synthesis of Formula (II)), is optional. In yet other embodiments, glassware and spin bars are optionally dried (e.g., before synthesis of Formula (II)).

In some embodiments, the activated Z can be reacted with Formula (II) to provide a compound of the invention (e.g., Formula (I)). In certain embodiments, the pH of the reaction solution is from about 1.0 to about 7.0, from about 2.0 to about 5.0, from about 3.0 to about 4.0, about 1.0, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.5, about 6.0, about 6.5, or about 7.0. In other embodiments, the reaction solution comprises a buffer system (e.g., comprising 0.1 M sodium acetate or comprising 0.1 M sodium acetate with 150 mM sodium chloride). In certain embodiments, the activated Z is in a solution that is cooler than room temperature (e.g., in an ice bath). In other embodiments, Formula (II) is dissolved in a polar solvent prior to its addition to the activated Z; the dissolution of Formula (II) can be accomplished with any suitable polar solvent, such as but not limited to polar aprotic solvents, acetonitrile, acetone, THF, polar protic solvents, methanol, or ethanol. In yet other embodiments, the dissolved Formula (II) is added so as not to exceed about 5%, about 10%, about 15%, about 20%, about 25%, or about 30% volume/volume of the total reaction solution. In certain embodiments, after Formula (II) (e.g., dissolved Formula (II)) is added the activated Z, the reaction is allowed to take place for from about 4 hours to about 48 hours, about 4 hours, about 8 hours, about 12 hours, about 16 hours, about 24 hours, about 36 hours, or about 48 hours. In some embodiments, the reaction takes place at a temperature of from about −5° C. to about 20° C., about −5° C., about 0° C., about 5° C., about 10° C., about 15° C., or about 20° C.

In certain embodiments, the compound of the invention (e.g., Formula (I)) can optionally be recovered. Recovery can occur using any suitable method including but not limited to HPLC (e.g., reverse phase), LC, precipitation, centrifugation, column chromatography (e.g., size exclusion chromatography or ion exchange chromatography), use of silica gel, or combinations thereof. In some embodiments, recovery of the compound of the invention (e.g., Formula (I)) can be accomplished using a butyl sepharose column with a decreasing concentration of ammonium sulfate, followed by size exclusion chromatography (e.g., sephadex G-25) using water, dilute acetic acid, ammonium acetate, or combinations thereof.

In other embodiments, the compound of the invention (e.g., Formula (I)) can be lyophilized. In yet other embodiments, a lyophilized composition comprising the compound of the invention (e.g., Formula (I)) can further comprise any suitable substance to stabilize the compound of the invention (e.g., Formula (I)) such as, but not limited to one or more simple carbohydrates (e.g., sucrose, mannitol, trehalose, or a combination thereof).

The presently disclosed subject matter is further illustrated by the following specific but non-limiting examples. The following examples may include compilations of data that are representative of data gathered at various times during the course of development and experimentation related to the present invention.

EXAMPLES

Example 1: Synthesis of Ansamitocin P3 Thiol (AP3-SH)—Method A

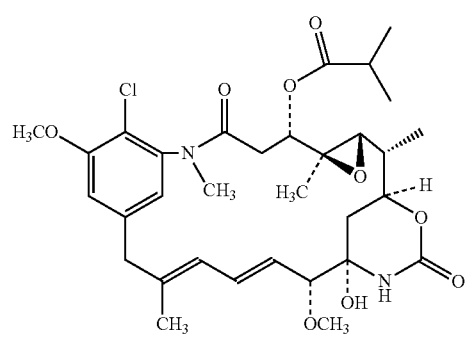

Chemical Formula: $C_{32}H_{43}ClN_2O_9$
Molecular Weight: 635.14

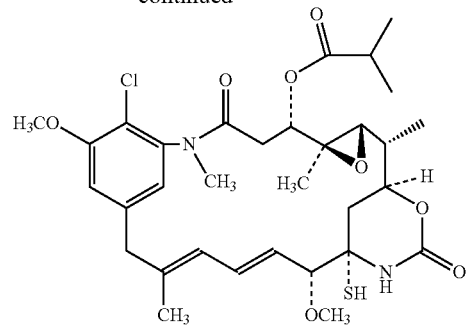

Chemical Formula: $C_{32}H_{43}ClN_2O_8S$
Molecular Weight: 651.21

Ansamitocin P3 (AP3 or AP-3) (MedChemExpress, LLC, Monmouth Junction, NJ US) (19 mg) was weighed in a glass screw cap vial. Separately, phosphorous pentasulfide ($P_2S_5$) (7.3 mg) was weighed in a screw cap vial and equipped with a small spin bar. The vial tops were secured with filter paper and both vials were dried under high vacuum with warming to 40° C. for 1 hour. Meanwhile, pyridine was dried in a Stark apparatus with calcium hydride for several hours. The dissolved phosphorous pentasulfide was then dissolved in about 2 mL dry pyridine with screw cap on (15 min). The AP3 was dissolved in about 1 mL dry pyridine and added to the $P_2S_5$ solution, which was mixed with screw cap on for 30 min at room temperature, and then placed in a heating oil bath at 65° C. for 3 hours. The solution was transferred to a round bottom flask and evaporated on a rotovap at 60° C. The residue was dissolved in a mixture of HPLC solvents A and B 1:1. (HPLC Solvents A—0.01% TFA, Solvent B—80% Acetonitrile in 0.01% TFA) and purified by preparative HPLC using a linear gradient of 10% B to 100% B. Product eluted around 74% B. Pure fractions were pooled and lyophilized.

Example 2: Synthesis of Ansamitocin P3 Thiol (AP3-SH)—Method B

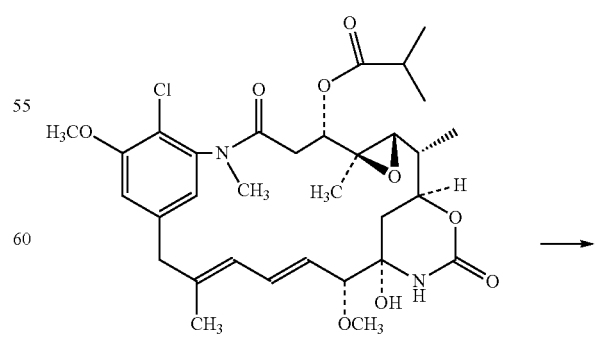

Chemical Formula: $C_{32}H_{43}ClN_2O_9$
Molecular Weight: 635.14

-continued

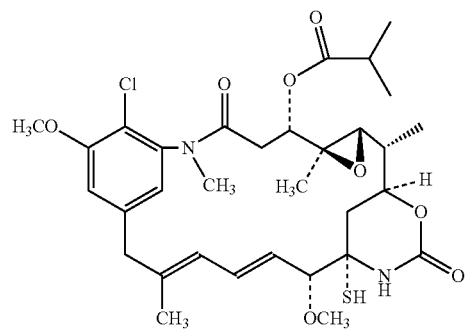

Chemical Formula: $C_{32}H_{43}ClN_2O_8S$
Molecular Weight: 651.21

Ansamitocin P3 (AP3 or AP-3) (MedChemExpress, LLC, Monmouth Junction, NJ US) (10 mg) was weighed in a glass screw cap vial and secured with a filter paper top; the vial was dried under high vacuum with warming to 40° C. for 1 hour. The dried AP3 was then dissolved in 50 mL dry methylene chloride and added to a dried 2 neck round bottom flask equipped with dropper funnel assembly under a stream of argon and bubbler to exclude moisture. $H_2S$ gas was then bubbled into the solution during cooling on an ice bath. Dry methylene chloride (5 ml) and TFA (1 ml) were added to the dropper funnel and the mixture was slowly dripped into the AP3 solution and allowed to mix overnight. The solution was transferred to a round bottom flask and evaporated to dryness at room temperature. The residue was dissolved in a mixture of HPLC solvents A and B 1:1. (HPLC Solvents A—0.01% TFA, Solvent B—80% Acetonitrile (ACN) in 0.01% TFA) and purified on preparative HPLC using a linear gradient of 10% B to 100% B. Product eluted around 74% B. Pure fractions were pooled and lyophilized.

Example 3: Synthesis of Human Serum Albumin (HSA)—AP3 Conjugate

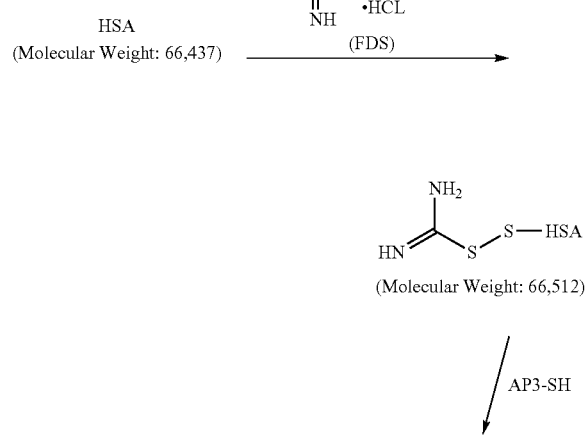

-continued

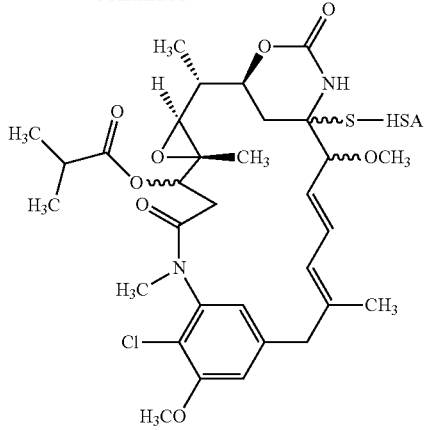

(Molecular Weight: 67,086.21)

Recombinant human serum albumin (100 mg) (Wuhan Healthgen Biotechnology Corp., Wuhan, China) was dissolved in 3 mL ice cold 0.1M acetate buffer (pH 3.5 with 150 mM NaCl) in a glass culture tube and placed in an ice bath. Formamidine disulfide (FDS) (3 mg) was placed in a culture tube and dissolved in 500 μL ice cold 0.1 M acetate buffer and placed on ice. The FDS solution was then added to the albumin while mixing. After 5 minutes, the excess FDS was separated from activated albumin using Sephadex G-25 eluted with 0.1M acetate buffer. The purified and activated albumin was cooled to 0° C. in an ice bath. Ansamitocin P3 (AP3) (1.05 equivalents of thiol) was dissolved in 200 μL acetonitrile and added to the ice cold isothiourea-albumin while mixing; it was then placed in a refrigerator overnight. The reaction was monitored using HPLC. The reaction reached about 60-80% completeness and the product was purified using Sephadex G-25 size exclusion chromatography using distilled water as eluent.

Example 4: Synthesis of Canine Serum Albumin (CSA)—AP3 Conjugate

Canine serum albumin (Animal Blood Resources International, Stockbridge, MI US) (100 mg) was dissolved in 4 mL ice cold PBS (pH 7.4) in a 50 mL falcon tube and placed in an ice bath. In a separate tube, 3.5 μL of mercaptoethanol was added to 1 mL PBS and cooled in an ice bath and then added to the solution of canine serum albumin, mixed and placed in the refrigerator overnight. The reactants were purified on Sephadex G-25 using 0.1M acetate buffer. Formamidine disulfide (FDS) (4 mg) was weighed in a culture tube and dissolved in 500 μL ice cold 0.1M acetate buffer and placed on ice and added at once to the albumin while mixing. After 5 minutes, excess FDS was separated from activated isothiourea-albumin using Sephadex G-25 and 0.1M acetate buffer. AP3 (1.05 equivalents), dissolved in 200 μL acetonitrile, was then added to ice cold isothiourea-albumin while mixing and placed in a refrigerator overnight. The reaction was monitored using HPLC. The reaction reached about 60-80% completeness and the product was purified using Sephadex G-25 size exclusion chromatography using distilled water as a solvent.

Example 5: Synthesis of Feline Serum Albumin (FSA)—AP3 Conjugate

Feline serum albumin (BioWorld, Dublin, OH US) (100 mg) was dissolved in 4 mL ice cold PBS (pH 7.4) in a 50 mL falcon tube and placed in an ice bath. In a separate tube, 3.5 µL of mercaptoethanol was added to 1 mL PBS and cooled in an ice bath and then added to the solution of feline serum albumin, mixed and placed in the refrigerator overnight. The reactants were purified on Sephadex G-25 using 0.1M acetate buffer. Formamidine disulfide (FDS) (4 mg) was weighed in a culture tube and dissolved in 500 µL ice cold 0.1M acetate buffer and placed on ice and added at once to the albumin while mixing. After 5 minutes, excess FDS was separated from activated isothiourea-albumin using Sephadex G-25 and 0.1M acetate buffer. AP3 thiol (1.05 equivalents), dissolved in 200 µL acetonitrile, was then added to ice cold isothiourea-albumin while mixing and placed in a refrigerator overnight. The reaction was monitored using HPLC. The reaction reached about 60-80% completeness and the product was purified using Sephadex G-25 size exclusion chromatography using distilled water as a solvent.

Example 6: Synthesis of Equine Serum Albumin (ESA)—AP3 Conjugate

Equine serum albumin (Abcom, Boston, MA US) (100 mg) was dissolved in 4 mL ice cold PBS (pH 7.4) in a 50 mL falcon tube and placed in an ice bath. In a separate tube, 3.5 µL of mercaptoethanol was added to 1 mL PBS and cooled in an ice bath and then added to the solution of equine serum albumin, mixed and placed in the refrigerator overnight. The reactants were purified on Sephadex G-25 using 0.1M acetate buffer. Formamidine disulfide (FDS) (4 mg) was weighed in a culture tube and dissolved in 500 µL ice cold 0.1M acetate buffer and placed on ice and added at once to the albumin while mixing. After 5 minutes, excess FDS was separated from activated isothiourea-albumin using Sephadex G-25 and 0.1 M acetate buffer. AP3 thiol (1.05 equivalents), dissolved in 200 µL acetonitrile, was then added to ice cold isothiourea-albumin while mixing and placed in a refrigerator overnight. The reaction was monitored using HPLC. The reaction reached about 60-80% completeness and product was purified using Sephadex G-25 size exclusion chromatography using distilled water as a solvent.

Example 7: Synthesis of Bovine Serum Albumin (BSA)—AP3 Conjugate

Bovine serum albumin (Sigma Aldrich, St. Louis, MO US) (100 mg) was dissolved in 4 mL ice cold PBS (pH 7.4) in a 50 mL falcon tube and placed in an ice bath. In a separate tube, 3.5 µL of mercaptoethanol was added to 1 mL PBS and cooled in an ice bath and then added to the solution of bovine serum albumin, mixed and placed in the refrigerator overnight. The reactants were purified on Sephadex G-25 using 0.1M acetate buffer. Formamidine disulfide (FDS) (4 mg) was weighed in a culture tube and dissolved in 500 µL ice cold 0.1M acetate buffer and placed on ice and added at once to the albumin while mixing. After 5 minutes, excess FDS was separated from activated isothiourea-albumin using Sephadex G-25 and 0.1M acetate buffer. AP3 thiol (1.05 equivalents), dissolved in 200 µL acetonitrile, was then added to ice cold isothiourea-albumin while mixing and placed in a refrigerator overnight. The reaction was monitored using HPLC. The reaction reached about 60-80% completeness and product was purified using Sephadex G-25 size exclusion chromatography using distilled water as a solvent.

Example 8: Lyophilization of AP3-BSA Conjugate

Mannitol (~150 mg) and 100 mg sucrose was added to the purified AP3-BSA conjugate and was gently mixed until everything dissolved. Then this solution was placed in a culture vial, which was turned in a bath of liquid nitrogen until frozen solid. The vial was then placed on a lyophilizer for two days to yield a fluffy white powder.

Example 9: CCK8 Assay Method (In Vitro Cell Proliferation Assay)

Cell viability assays were conducted using the cell counting Kit-8 (CCK-8; Dojindo, Kumamoto, Japan) following the manufacturer's protocol. Briefly, cells were seeded in 96-well cell culture plates at a cell density of $8 \times 10^3$ cells per well, with different concentrations ($10^{-13}$, $10^{-12}$, $10^{-11}$, $10^{-10}$, $10^{-9}$, $10^{-8}$, $10^{-7}$, $10^{-6}$ M) of compounds added to each well, respectively. The content in wells were mixed well. The plates were incubated at 37° C. for 72 h. Then 10 µL of CCK-8 solution was added and the plates were incubated for another 1-4 h. The OD values were measured at 450 nm using a microplate reader (BioTek, USA).

FIGS. 1-8 show that compounds of the invention (e.g., Compounds I-1 and I-3) provide similar potencies compared to AP3 when tested according to this method in several human and animal cancer cell lines.

Example 10: Xenograft Mouse Model (In Vivo Anti-Tumor Assay)—Lymphoma Tumor

Female BALB/c nude mice aged at 4-6 weeks-old were purchased (Tyercan, Ltd, Shenzhen) and reared in the laboratory animal facility for one week to adapt to the new environment. A total of $5 \times 10^6$ human gastric tumor SGC-7901 cells (200 µl) were inoculated into the right flank of each mouse by subcutaneous injection. When the tumor sizes reached 100-300 mm$^3$ (tumor volume=$0.5 \times$Length$\times$Width$^2$), tumor-carrying mice in the experimental group were given (via tail vein injection) a first dose (at day zero) of 100 µl of AP3-HSA 200 mg/kg and a second dose (at day 14) of 150 mg/kg. A control group was injected with 100 µl of AP-3 containing 0.4 mg of AP-3 on days 0 and 14 in a similar fashion. 100 µl of normal saline was injected via the tail vein in a second control group on the same days. Tumor volumes were measured and mouse bodies were weighed twice a week since the first administration.

Figure 9:
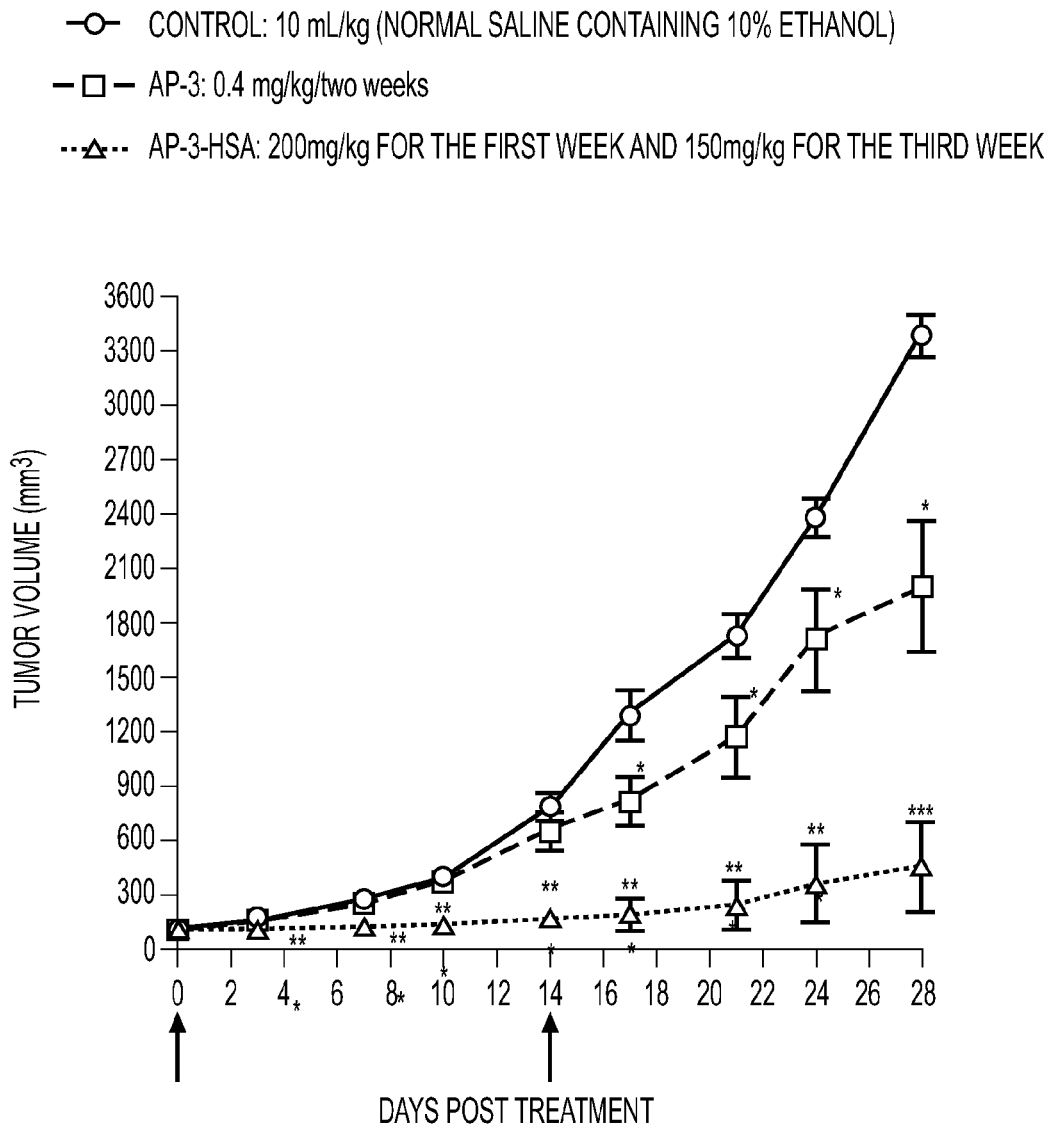
FIG. 9. Effects of AP3 and Compound I-1 on the growth of human gastric tumor SGC-7901 cells injected sc into nude mice on day 0. Compounds were injected into the tail veins at day 0 (200 mg/kg) and at day 14 (150 mg/kg) for Compound I-1 and at day 0 and day 14 for AP3. AP3 was only marginally effective at this dose level compared to controls, whereas the Compound I-1 was effective throughout the study period.
Figure 10:
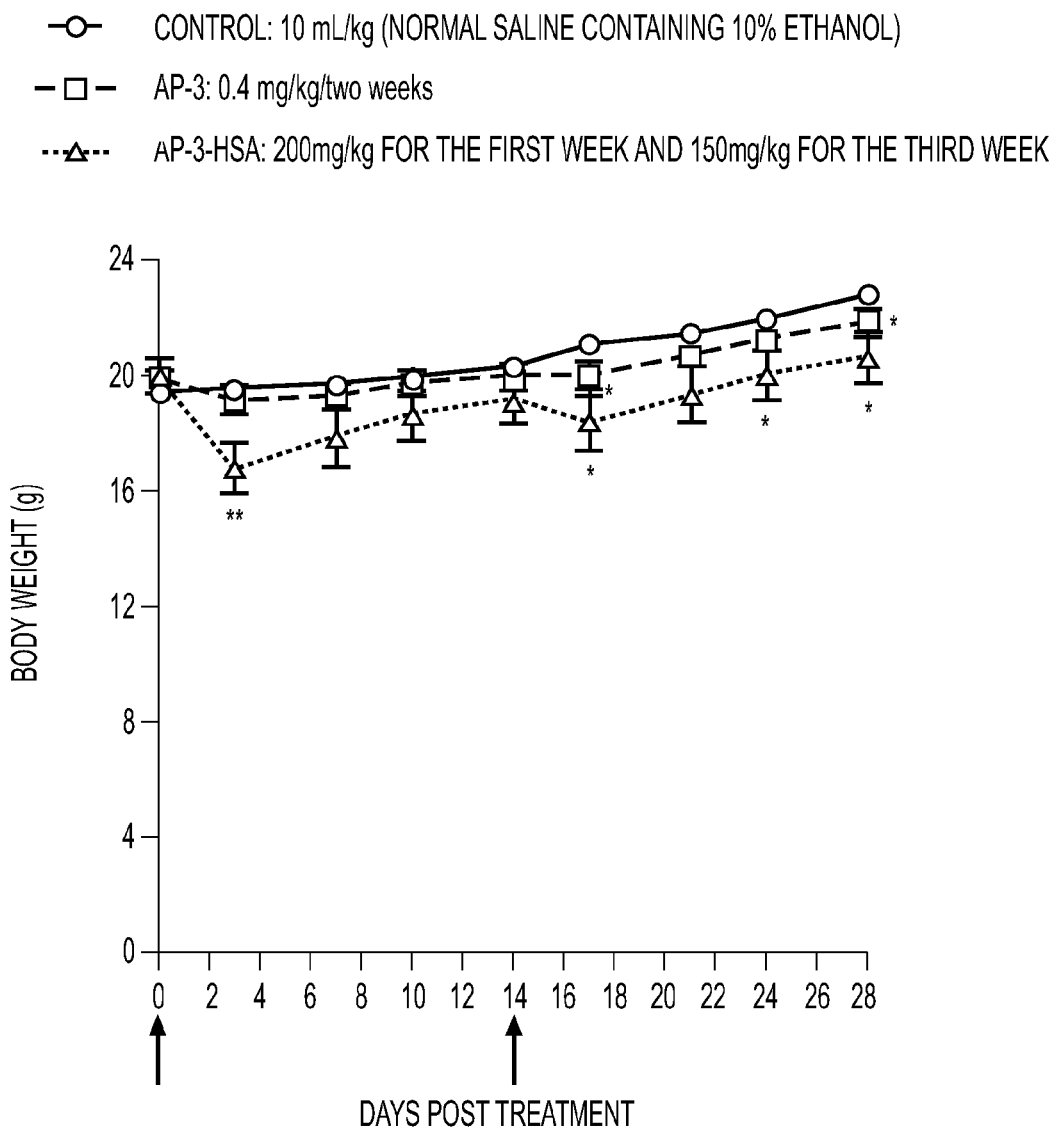
FIG. 10. Effects of AP3 and Compound I-1 on the body weights of nude mice treated under the protocols of the experiment described in FIG. 9 where compounds were injected into the tail veins at day 0 (200 mg/kg) and at day 14 (150 mg/kg) for Compound I-1 and at day 0 and day 14 for AP3. AP3 was only marginally effective at this dose level compared to controls, whereas Compound I-1 was effective throughout the study period. Decreases in body weight were observed for the Compound I-1 treated group.

FIGS. 9-10 show that compound I-1 was more effective at treating gastric tumor growth compared to AP3, while compound I-1 resulted in statistically insignificant decreases in body weight suggesting acceptable toxicity levels.

Example 11: Xenograft Mouse Model (In Vivo Anti-Tumor Assay)—Gastric Tumor

Female SCID mice (Tyercan, Ltd, Shenzhen) aged at 4-6 weeks-old were purchased and reared in the laboratory animal facility for one week to adapt to the new environment. A total of $5 \times 10^6$ human U-937 lymphoma tumor cells (200 µl) were inoculated into the right flank of each mouse by subcutaneous injection. When the tumor sizes reached 100-300 mm$^3$ (tumor volume=$0.5 \times$Length$\times$Width$^2$), tumor-carrying mice in the experimental group were given (via tail vein injection) 100 µl of AP3-HSA at a dose of 300 mg/kg on days 0, 7, 15, and 21. A control group was injected with 100 µl of AP-3 containing 0.5 mg of AP-3 on days 0, 7, 15 and 21 in a similar fashion. 100 µl of normal saline was injected via the tail vein in a second control group on the same days. Tumor volumes were measured and mouse bodies were weighed twice a week since the first administration.

Figure 11:
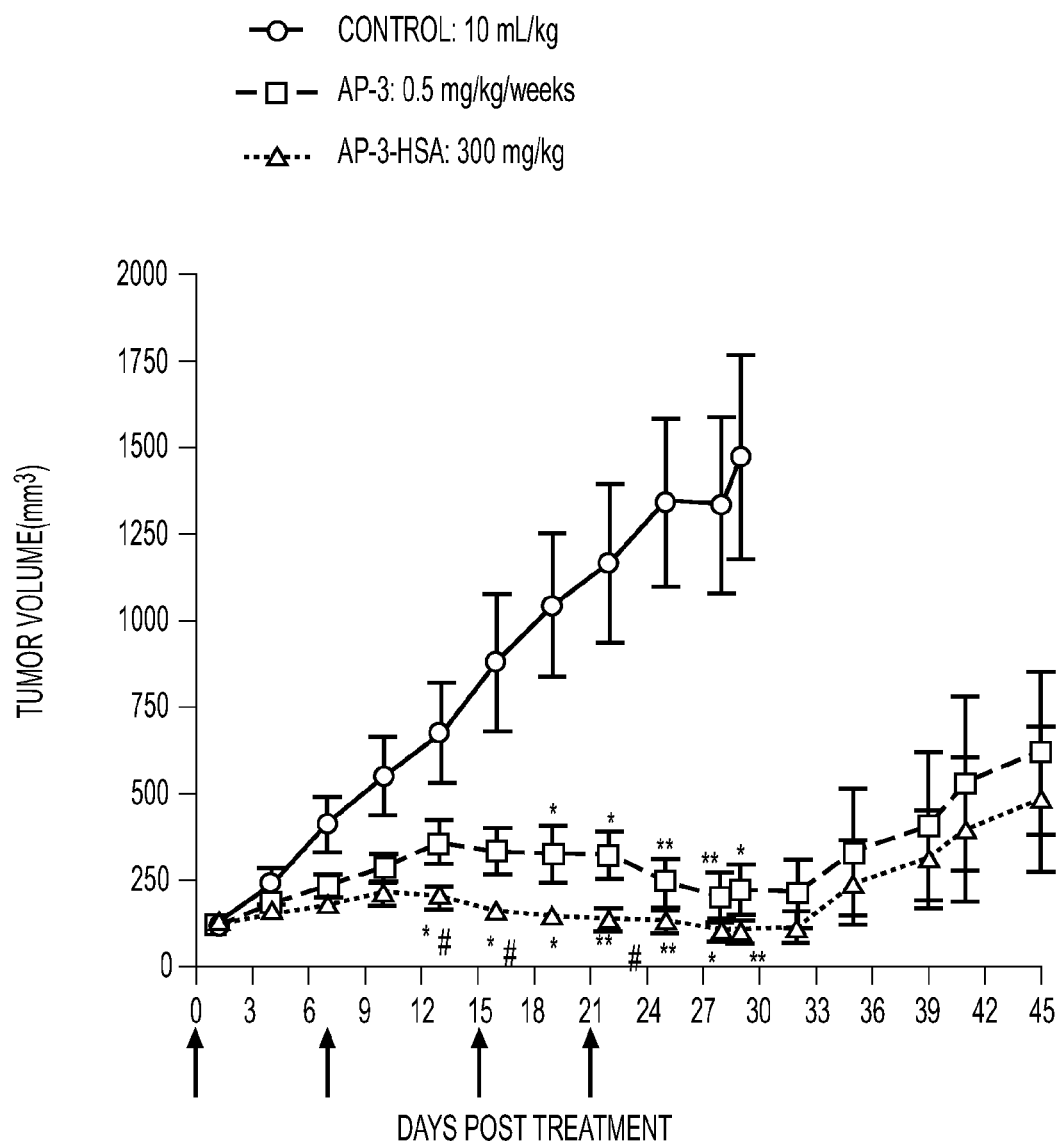
FIG. 11. Effects of AP3 and Compound I-1 on the growth of human U-937 lymphoma tumor cells injected sc into SCID mice on day 0. AP3 (0.5 mg/kg) was injected into the tail veins at days 0 and 15 and Compound I-1 (300 mg/kg) at days 0, 7, 15, and 21. Compound I-1 was more effective than AP3. Compound I-1 resulted in almost complete inhibition tumor growth up until 30 days.
Figure 12:
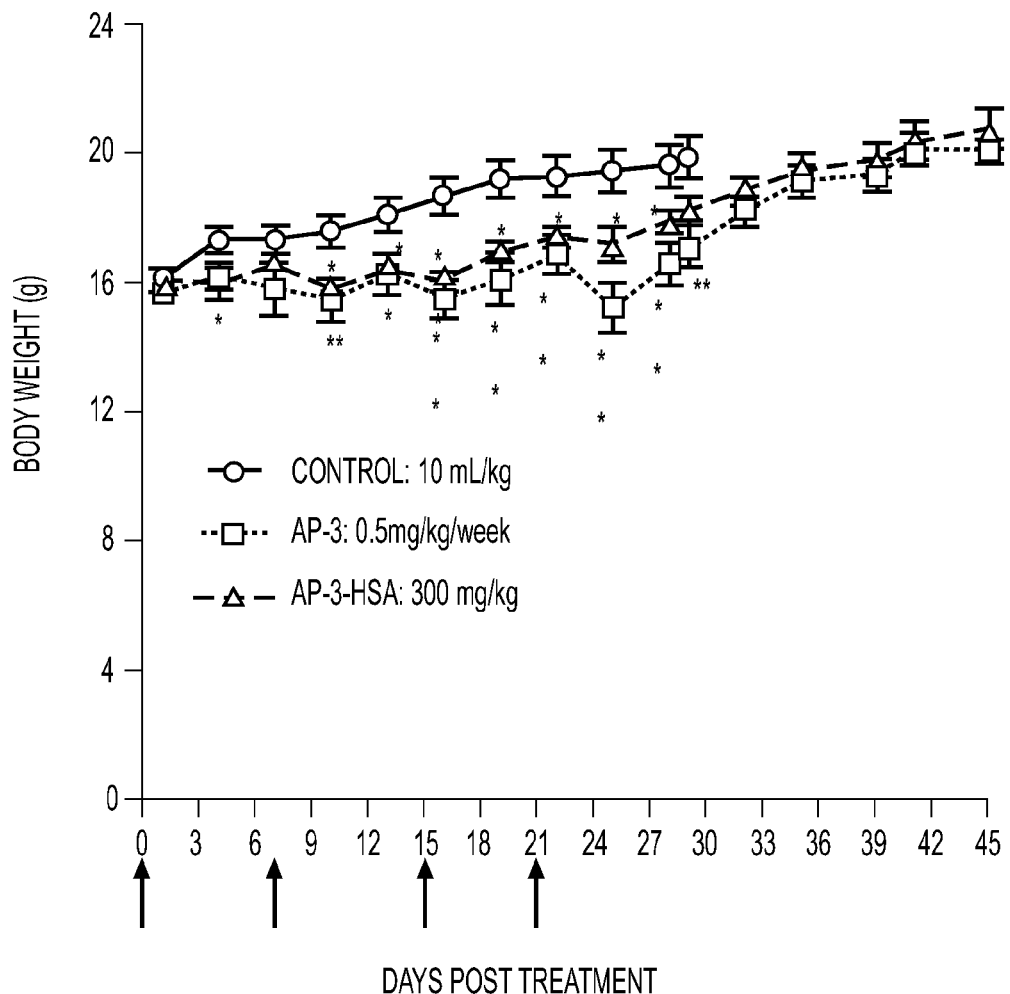
FIG. 12. Effects of AP3 and Compound I-1 on the body weights of SCID mice treated under the protocols of the experiment described in FIG. 11. Mouse weight losses were observed for both treatment groups during the period. Body weights returned to normal about a week after the final injections.

FIGS. 11-12 show that compound I-1 was more effective at treating lymphoma tumor growth compared to AP3, while both AP3 and compound I-1 resulted in decreases in body weight using this higher dosing protocol.

Example 12: Surface Plasmon Resonance Affinity Measurement of Thio-AP-3-HSA with the Human FcRn Protein Receptor Recombinant HSA was purchased from Wuhan Heyuan Biotechnology Co., Ltd. Recombinant human FcRn (6 his-tagged) was from Novoprotein. FcRn protein was immobilized on the flow channel 4 (FC4) of a CM5 sensor chip via amine coupling. First, the carboxymethylated dextran layer on FC3 and FC4 were activated by freshly prepared mixture of 0.4 M EDC and 0.1 M NHS (1:1, v/v). 170 µL of the mixture was introduced into FC4 at a flow rate of 20 µL/min. The ligand was diluted with pH 4.4 sodium acetate buffer to a final concentration of 100 µg/mL and coupled to the activated FC4 surfaces by its free amines at a flow rate of 10 µL/min for 100 µL. After coupling, 1 M ethanolamine was added to block unreacted sites for FC3 and FC4 at a flow rate of 20 µL/min for 170 µL. HSA as control was observed at ranges of concentrations (1485 nM, 742 nM, 371 nM, 1485 nM, 2970 nM and 5940 nM) and AP-3-HSA as experimental sample at ranges of concentrations (448 nM, 224 nM, 3582 nM, 1791 nM, 1791 nM and 896 nM) were injected into FC4 and FC3 at a flow rate of 20 µL/min for more than 2 minutes with 60 µL. The disassociation time was set to 2 minutes in the curve fitting process.

Figure 13:
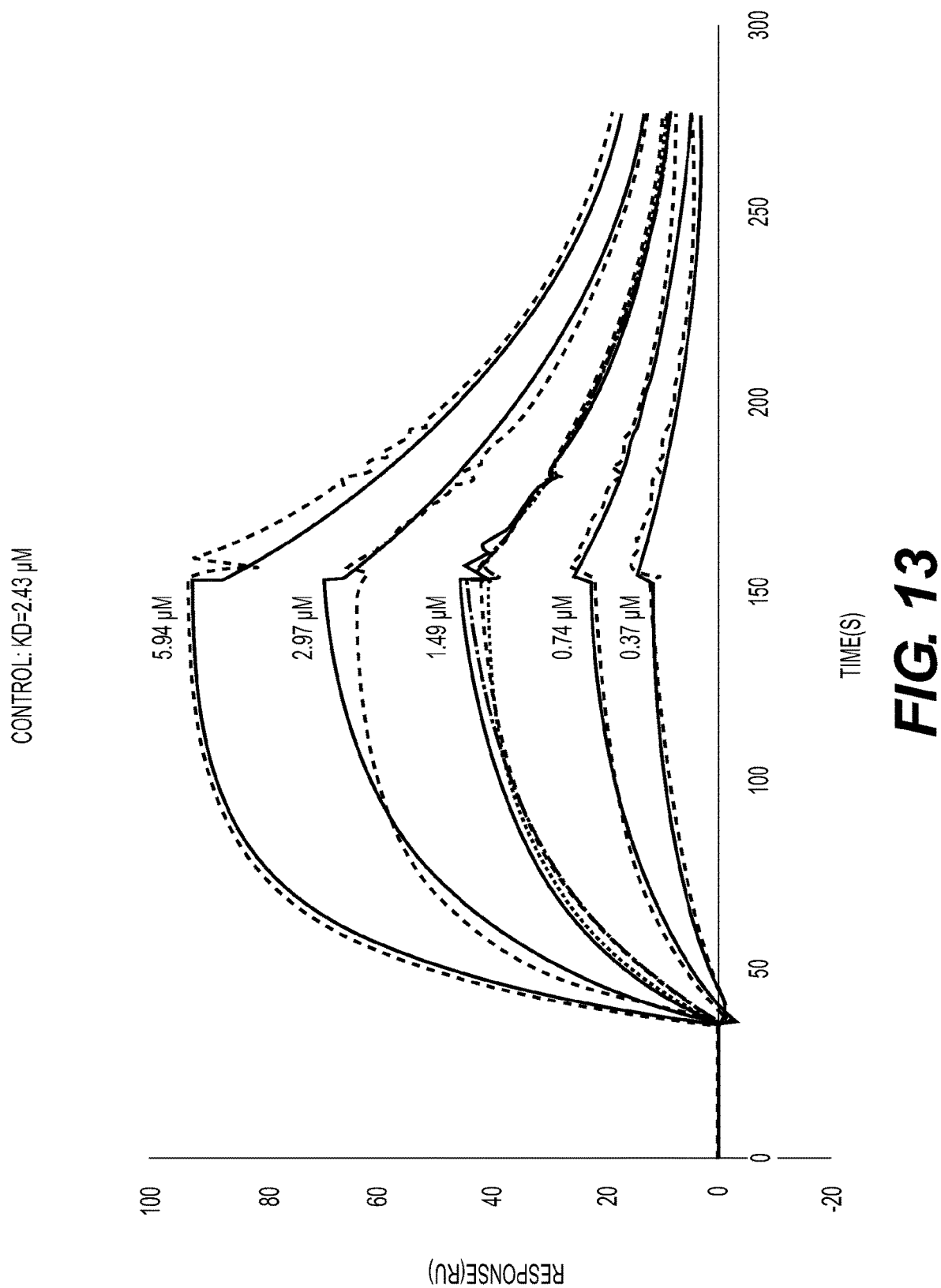
FIG. 13. The affinities of recombinant HSA for the recombinant human FcRn receptor using surface plasmon resonance microscopy shows that recombinant HSA binds in a pH dependent manner.
Figure 14:
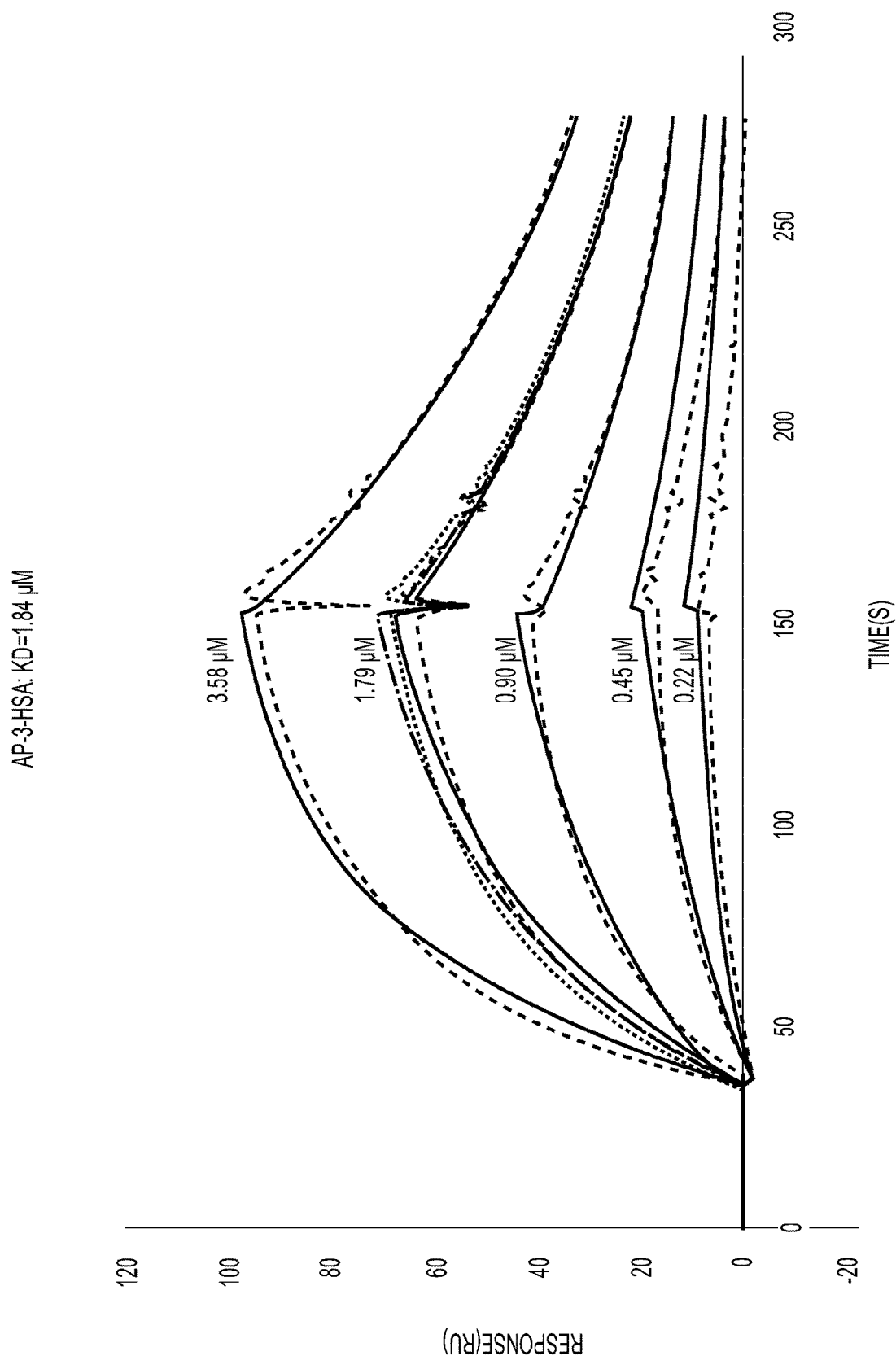
FIG. 14. The affinities of Compound I-1 for the recombinant human FcRn receptor using surface plasmon resonance microscopy shows that Compound I-1 binds in a pH dependent manner. HSA (from FIG. 13) and Compound I-1 exhibited similar concentration-dependent binding and response rates.

FIGS. 13-14 show that HSA and compound I-1 exhibited similar concentration dependent binding and response rates, for binding to recombinant human FcRn receptor suggesting no deleterious structural effects on the HSA protein.

Example 13: Synthesis of Maytansine-SH

Reaction Formula

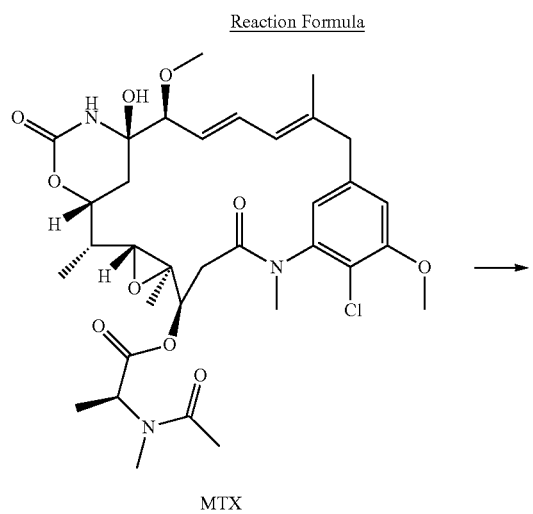

MTX

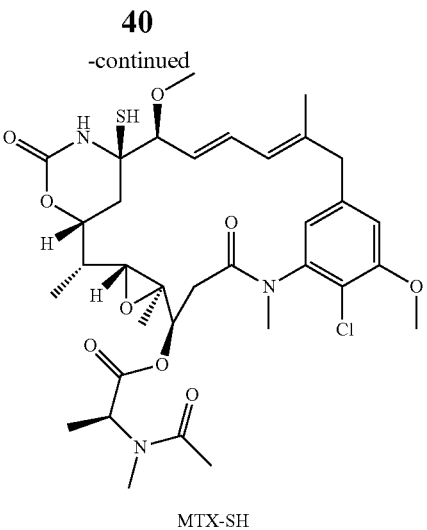

MTX-SH

Process

Pyridine was dried over $CaH_2$ in room temperature for 16 hours. When the moisture becomes less than 0.1%, the drying was finished, and pyridine was filtered for next step. Otherwise, the drying time should be extended or $CaH_2$ should be added until the moisture conforms to the standard.

300 mg of Maytansine (MTX) (1.0 eq.) was placed in 50 mL single-mouth bottle and dried in vacuum at 55° C. for 4.0 h. 360 mg of $P_2S_5$ (3.4 eq.) was placed in 50 mL single-mouth bottle and dried in vacuum at 58° C. for 4.0 h.

$P_2S_5$ was cooled to 20° C.-30° C., 10 mL of pyridine was added and the mixture was stirred at room temperature for 30 min.

Maytansine was dissolved with 10 mL of pyridine and resulting solution was injected into $P_2S_5$ solution and stirring was continued at room temperature for 30 min.

The reaction solution was placed under nitrogen, then heated up to 60° C. for 2-4 h. In-process control was performed until the level of Maytansine becomes less than 1%.

The solution was concentrated under reduced pressure, the residue was dissolved in methanol and purified by Prep-HPLC.

The purified product was lyophilized to afford Maytansine-SH.

| Lot | Quantity of Maytansine-SH (mg) | Purity |
|-----|-------------------------------|--------|
| 13A | 45 | 97.95% |
| 13B | 86 | 99.49% |
| 13C | 267 | 99.20% |

Analytical Procedure

Column: Agilent ZORBAX SB-C18 (150*4.6 mm 5 µm)

Injection Volume: 10 µL

Flow rate: 1.0 mL/min

Column temperature: 30° C.

Detected wavelength: 254 nm

Mobile phase A: 0.01% trifluoroacetic acid (TFA)—$H_2O$

Mobile phase B: 0.01% TFA-$H_2O$:acetonitrile (CAN)= 2:8

Gradient Procedure

| Time (min) | A (%) | B (%) |
|---|---|---|
| 0 | 90 | 10 |
| 12 | 0 | 100 |
| 15 | 0 | 100 |
| 16 | 90 | 10 |
| 20 | 90 | 10 |

Diluent: Methanol

Sample solution: Take 3 drops of reaction solution into a 10 mL centrifuge tube, add 1 ml methanol to dissolve, shake well and filter.

Example 14: Coupling of Maytansine-HSA and Lyophilization

Solution Preparation:
100 mM PBS (Buffer 1)

Weigh 2.6218 g of sodium dihydrogen phosphate, 5.5177 g of disodium hydrogen phosphate and 2.922 g of sodium chloride and dissolve them into 400 mL of ultrapure water. Adjust the pH to 7.4 with 2M NaOH, then use ultrapure water to fill to 500 mL.
0.1M Acetate, 0.15M NaCl (Buffer 2)

Weigh 3.319 g of sodium acetate, 58.585 g of glacial acetic acid and 87.660 g of sodium chloride, and dissolve in 8000 mL of ultrapure water. Adjust pH to 3 with 20% AcOH, and then use ultrapure water to fill to 10000 mL.
20 mM Histidine. 4% Mannitol (Buffer 3)

Weigh 15.515 g of histidine and 200.00 g of mannitol, dissolve in 4000 mL of ultrapure water, adjust pH to 6.5 with dilute hydrochloric acid, and then use ultrapure water to fill to 5000 mL.
20 mM Histidine, 4% Mannitol, 30% Sucrose (Buffer 4)

Weigh 0.3103 g of histidine, 4.00 g of mannitol and 30.00 g of sucrose, dissolve in 80 mL of ultrapure water, adjust pH to 6.5 with dilute hydrochloric acid, and then use ultrapure water to fill to 100 mL.
20 mM Histidine, 4% Mannitol, 1% Sucrose (Buffer 5)

Weigh 3.103 g of histidine, 40.000 g of mannitol and 10.00 g of sucrose, dissolve in 800 mL of ultrapure water, then use ultrapure water to fill to 1000 mL to obtain alkali solution of Histidine. Weigh 4.193 g of histidine hydrochloride, 40.000 g of mannitol and 10.00 g of sucrose, dissolve in 800 mL of ultrapure water, then use ultrapure water to fill to 1000 mL to obtain acidic solution of Histidine. Add the acidic solution of histidine to the alkali solution of histidine slowly until the pH is 6.5 to obtain buffer 5.

Procedure

Take an appropriate amount of liquid HSA and dissolve in buffer 1, measure its concentration.

Reduction

Reduction was carried out according to the conditions in Table 14A, noting that buffer was added first, followed by DTT (dithiothreitol).

TABLE 14A

| HSA (mg) | Volume (mL) | Concentration (mg/mL) | DTT/HSA Mole Ratio | $V_{Buffer\ 1}$ (mL) | $V_{DTT}$ (mL) | Reduction Time (h) | Reduction Temp. (° C.) |
|---|---|---|---|---|---|---|---|
| 3809.091 | 197.260 | 19.310 | 1.5 | 166.27 | 17.374 | 1 | 22 |

Add 197.260 mL of HSA (3809.091 mg, 57.334 μmol, 1 eq, 19.310 mg/mL) to 1 L Schott bottle, control temperature between 20-24° C., add 166.27 mL of buffer 1 with magnetic stirring, 17.374 mL of DTT (5 mM, 86.001 μmol, 1.5 eq) aqueous solution was slowly added, and then transfer to a shaker, maintain at 22° C. and react at 90 rpm for 1 h. At the end of the reaction, the net weight of the reaction solution was weighed, and the pH was adjusted to 3.5-4.0 with 20% AcOH (w/w) aqueous solution of ⅛ of the net weight of the reaction solution, and then buffer exchange was done.

Buffer Exchange:

a) Set the pump speed to 160 rpm (320 mL/min), washed with water, and then washed with alkali solution, cycled for 30 min.

b) Wash with water, rinse the membrane with buffer 2 until the pH of the solution through the end is consistent with that of the buffer.

c) Set pump speed 160 rpm (320 mL/min), transmembrane pressure (TMP): 0.25 bar, exchange solution for 10 DV (Diavolume).

d) buffer 2 was used for buffer exchange, and the pump speed was set to 160 rpm (320 mL/min), TMP: 0.25 bar, exchanged solution for 10 DV.

e) 298.495 mL was afforded, its concentration was 12.712 mg/mL and contained protein 3,794.468 mg.

Modification

Modification was carried out according to the conditions in Table 14B, noting that buffer 2 was added first, followed by Formamidine disulfide (FDS).

TABLE 14B

| HSA-red (mg) | Volume (mL) | Concentration (mg/mL) | FDS/HSA-red Mole Ratio | $V_{Buffer2}$ (mL) | $V_{FDS}$ (mL) | Reduction Time (h) | Modification Temp. (° C.) |
|---|---|---|---|---|---|---|---|
| 3797.610 | 298.75 | 12.712 | 12.5 | 51.547 | 29.464 | 0.5 | 10 |

Added 298.75 mL of HSA-red (3797.610 mg, 57.161 μmol, 1 eq, 12.712 mg/mL) to 1 L Schott bottle, control temperature between 5-10° C., add 51.547 mL of buffer 2 with magnetic stirring, 29.464 mL of FDS (25 mM, 714.512 μmol, 12.5 eq) aqueous solution was quickly added, and then transferred to a shaker, maintained at 10° C. and reacted at 90 rpm for 0.5 h. And then buffer exchange was done.

Buffer Exchange a) Set the pump speed to 160 rpm (320 mL/min), washed with water, and then washed with alkali solution, cycled for 30 min.

b) Washed with water, rinse the membrane with buffer 2 until the pH of the solution through the end is consistent with that of the buffer.

c) Set pump speed 160 rpm (320 mL/min), TMP: 0.25 bar, exchange solution for 10 DV (Diavolume).

d) buffer 2 was used for buffer exchange, and the pump speed was set to 160 rpm (320 mL/min), TMP: 0.25 bar, exchanged solution for 10 DV.

e) 257.96 mL was afforded, its concentration was 14.663 mg/mL and contained protein 3782.553 mg.

Coupling

Coupling was carried out according to the conditions in Table 14C, noting that Acetonitrile (ACN) was added first, followed by Maytansine-SH.

TABLE 14C

| HSA-mod (mg) | Volume (mL) | Concentration (mg/mL) | drug/ HSA-mod Mole Ratio | $V_{Buffer2}$ (mL) | $V_{ACN}$ (mL) | $V_{drug}$ (mL) | Coupling Time (h) | Modification Temp. (° C.) |
|---|---|---|---|---|---|---|---|---|
| 3756.159 | 256.160 | 14.663 | 2 | 81.894 | 26.176 | 11.386 | 16 | 10 |

Added 256.160 mL of HSA-mod(3756.159 mg, 56.473 μmol, 1 eq, 14.663 mg/mL) to 1 L Schott bottle, control temperature between 0-10° C., add 81.864 mL of buffer 2 with magnetic stirring, 26.176 mL of ACN was slowly added, 11.386 mL of ACN that contained Maytansine-SH (10 mM, 112.947 μmol, 2 eq) was slowly added, and then transferred to a shaker, maintained at 10° C. and reacted at 90 rpm for 16 h. At the end of the reaction, the net weight of the reaction solution was weighed, and the pH was adjusted to 6.0-6.5 with 1M Tris aqueous solution of 1/10 of the net weight of the reaction solution, and then buffer exchange was done.

Buffer Exchange a) Set the pump speed to 160 rpm (320 mL/min), washed with water, and then washed with alkali solution, cycled for 30 min.

b) Washed with water, rinse the membrane with buffer 3 until the pH of the solution through the end is consistent with that of the buffer.

c) Set pump speed 160 rpm (320 mL/min), TMP: 0.25 bar, exchange solution for 10 DV (Diavolume).

d) buffer 3 was used for buffer exchange, and the pump speed was set to 160 rpm (320 mL/min), TMP: 0.25 bar, exchanged solution for 10 DV.

Mixing with Excipients

The sample obtained after buffer exchange was diluted with buffer 3 to a concentration of 10.345 mg/mL, and buffer 4 of 1/29 of its volume was added, and filtered to afford the drug substance.

TABLE 14D

Results of the Drug Substance

| Lot | DAR(RP-HPLC) | Protein (mg/mL) | nr-CE(%) | SEC(%) |
|---|---|---|---|---|
| 14A | 0.79 | 10.5 | 96.8 | 95.4 |

Lyophilization

The drug substance (5.3 mL, density 1.020 g/cm$^3$) and Buffer 5 were added to cleaned and sterilized vials, then press the rubber plug to the half plug, turn on the lyophilizer.

Three days later, turn off the lyophilizer, vials were sealed with aluminum caps.

TABLE 14E

Results of the Lyophilization

| Lot | DAR (RP-HPLC) | Protein (mg/vial) | nr-CE (%) | SEC (%) | Moisture (%) |
|---|---|---|---|---|---|
| 14B | 0.77 | 52.666 | 96.3 | 95.6 | 0.7 |

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

In certain instances, sequences disclosed herein are included in publicly-available databases, such as GEN-BANK® and SWISSPROT. Unless otherwise indicated or apparent the references to such publicly-available databases are references to the most recent version of the database as of the filing date of this application.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties or functions sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

The invention claimed is:

1. A compound selected from the group consisting of Formula (I)

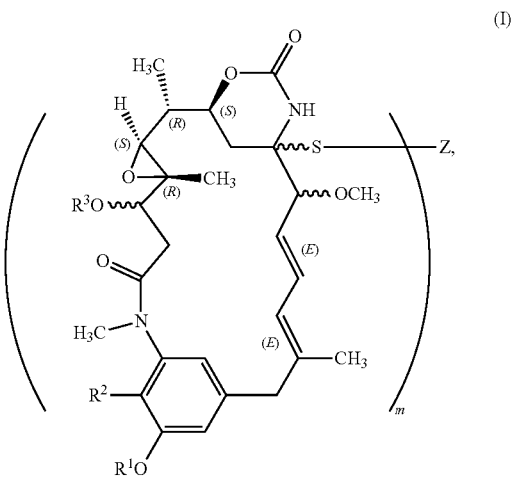

salts of Formula (I), optical isomers of Formula (I), geometric isomers of Formula (I), salts of optical isomers of Formula (I), salts of geometric isomers of Formula (I), and ether, ester or amide derivatives thereof, wherein
$R^1$ is selected from H, —COCH$_3$, carboxy (—CO$_2$H), ethynyl (—CCH), C$_1$-C$_8$ alkyl, C$_2$-C$_8$ alkenyl, C$_2$-C$_5$ alkynyl, methyl, ethyl, perfluorinated methyl, perfluorinated ethyl, C$_1$-C$_4$ alkylsulfonyl (—S(=O)$_2$-(C$_1$-C$_4$ alkyl)), and phenyl-(C$_1$-C$_4$ alkyl), which-COCH$_3$, carboxy (—CO$_2$H), ethynyl (—CCH), C$_1$-C$_8$alkyl, C$_2$-C$_8$ alkenyl, C$_2$-C$_8$ alkynyl, methyl, ethyl, C$_1$-C$_4$ alkylsulfonyl, or phenyl-(C$_1$-C$_4$ alkyl) can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, phenyl, perfluorinated methyl, perfluorinated ethyl, amino, C$_1$-C$_4$ alkanoylamino (—NH—CO—(C$_1$-C$_4$ alkyl)), C$_1$-C$_4$ alkoxy, benzyloxy (—O—CH$_2$-phenyl), oxo (=O), C$_2$-C$_5$ alkoxycarbonyl (—CO—O—(C$_2$-C$_5$ alkyl)), methylenedioxy (—O—CH$_2$-O—, with one or two attachment carbons), or C$_1$-C$_4$ alkylthio (—S—(C$_1$-C$_4$ alkyl));
$R^2$ is selected from H, allyl, vinyl, hydroxyl, C$_1$, Br, F, I, thiol, amino, nitro, cyano, C$_1$-C$_4$ alkyl, C$_1$-C$_4$ alkylnoic, phenyl, C$_1$-C$_2$ perfluorinated alkyl, alkyl amino, carboxy, acetyl, amido, and C$_1$-C$_3$ alkoxy;
$R^3$ is selected from H, C$_1$-C$_{18}$ alkyl, C$_2$-C$_{20}$ alkenyl, C$_2$-C$_{20}$ alkynyl, methyl, ethyl, perfluorinated methyl, perfluorinated ethyl, aryl, cycloalkyl, and -COR$_4$, which C$_1$-C$_{18}$ alkyl, C$_2$-C$_{20}$ alkenyl, C$_2$-C$_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, C$_1$-C$_4$ alkoxy, C$_2$-C$_4$ alkanoyl (—CO—(C$_2$-C$_4$ alkyl)), C$_2$-C$_4$ alkanoyloxy (—CO—O—(C$_2$-C$_4$ alkyl)), C$_2$-C$_4$ alkoxycarbonyl (—O—CO—(C$_2$-C$_4$ alkyl)), nitro, amino, mono(C$_1$-C$_4$ alkyl)amino, di(C$_1$-C$_4$ alkyl)amino, C$_1$-C$_4$ alkylthio (—S—(C$_1$-C$_4$ alkyl)), C$_1$-C$_4$ alkylsulfinyl (—SO—(C$_1$-C$_4$ alkyl)), $C_1$-$C_4$ alkylsulfonyl (—S(=O)$_2$-($C_1$-$C_4$ alkyl)), oxo (=O), thioxo (=S), or $C_1$-$C_4$ alkanoylamino (—CO—NH—($C_1$-$C_4$ alkyl));

$R^4$ is selected from $C_1$-$C_{18}$ alkyl, $C_2$-$C_{20}$ alkenyl, $C_2$-$C_{20}$ alkynyl, methyl, ethyl, perfluorinated methyl, perfluorinated ethyl, aryl, cycloalkyl, and

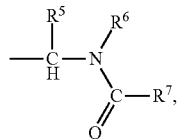

which $C_1$-$C_{18}$ alkyl, $C_2$-$C_{20}$ alkenyl, $C_2$-$C_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$-($C_1$-$C_4$ alkyl)), oxo (=O), thioxo (=S), or $C_1$-$C_4$ alkanoylamino (—CO—NH—($C_1$-$C_4$ alkyl));

$R^5$, $R^6$, and $R^7$ are the same or different and each is independently selected from $C_1$-$C_{18}$ alkyl, $C_2$-$C_{20}$ alkenyl, $C_2$-$C_{20}$ alkynyl, methyl, ethyl, perfluorinated methyl, perfluorinated ethyl, aryl, and cycloalkyl, which $C_1$-$C_{18}$ alkyl, $C_2$-$C_{20}$ alkenyl, $C_2$-$C_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$-($C_1$-$C_4$ alkyl)), oxo (=O), thioxo (=S), or $C_1$-$C_4$ alkanoylamino (—CO—NH—($C_1$-$C_4$ alkyl));

m is 1, 2, 3, 4, 5, 6, 7, 8, 9, or 10; and

Z is selected from an albumin, human serum albumin (HSA), bovine serum albumin (BSA), canine serum albumin (CSA), feline serum albumin (FSA), equine serum albumin (ESA), Domain I of HSA, Domain II of HSA, Domain III of HSA, an engineered albumin, mutants thereof, and fragments thereof.

2. The compound of claim 1, wherein, $R^1$ is selected from H, —COCH$_3$, carboxy (—CO$_2$H), ethynyl (—CCH), $C_1$-$C_4$ alkyl, $C_2$-$C_4$ alkenyl, $C_2$-$C_4$ alkynyl, methyl, ethyl, perfluorinated methyl, and perfluorinated ethyl, which-COCH$_3$, carboxy (—CO$_2$H), ethynyl (—CCH), $C_1$-$C_4$ alkyl, $C_2$-$C_4$ alkenyl, $C_2$-$C_4$ alkynyl, methyl, or ethyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, amino, $C_1$-$C_4$ alkoxy, or oxo.

3. The compound of claim 1, wherein $R^1$ is selected from the group consisting of H, —COCH$_3$, carboxy (—CO$_2$H), ethynyl (—CCH), methyl, ethyl, perfluorinated methyl, and perfluorinated ethyl.

4. The compound of claim 1, wherein $R^2$ is selected from the group consisting of H, $C_1$, Br, F, I, allyl, ethyl, methyl, and OH.

5. The compound of claim 1, wherein $R^2$ is H or $C_1$.

6. The compound of claim 1, wherein $R^3$ is selected from the group consisting of methyl, ethyl, propyl, butyl, pentyl, hexyl, heptyl, octyl, and nonyl.

7. The compound of claim 1, wherein $R^3$ is

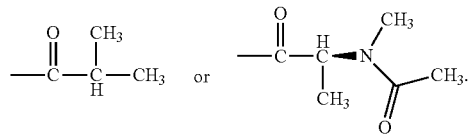

8. The compound of claim 1, wherein $R^4$ is selected from $C_1$-$C_{18}$ alkyl, $C_2$-$C_{20}$ alkenyl, $C_2$-$C_{20}$ alkynyl, methyl, ethyl, perfluorinated methyl, perfluorinated ethyl, aryl, and cycloalkyl, which $C_1$-$C_{18}$ alkyl, $C_2$-$C_{20}$ alkenyl, $C_2$-$C_{20}$ alkynyl, methyl, ethyl, aryl, or cycloalkyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$-($C_1$-$C_4$ alkyl)), oxo (=O), thioxo (=S), or $C_1$-$C_4$ alkanoylamino (—CO—NH—($C_1$-$C_4$ alkyl)).

9. The compound of claim 1, wherein $R^4$ is selected from $C_1$-$C_{10}$ alkyl, $C_2$-$C_{10}$ alkenyl, $C_2$-$C_{10}$ alkynyl, methyl, ethyl, perfluorinated methyl, and perfluorinated ethyl, which $C_1$-$C_{10}$ alkyl, $C_2$-$C_{10}$ alkenyl, $C_2$-$C_{10}$ alkynyl, methyl, or ethyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$-($C_1$-$C_4$ alkyl)), oxo (=O), thioxo (=S), or $C_1$-$C_4$ alkanoylamino (—CO—NH—($C_1$-$C_4$ alkyl)).

10. The compound of claim 1, wherein $R^4$ is selected from the group consisting of methyl, ethyl, propyl, butyl, pentyl, and hexyl.

11. The compound of claim 1, wherein $R^4$ is

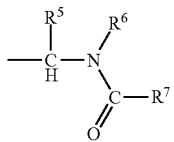

and $R^5$, $R^6$, and $R^7$ are the same or different and each is independently selected from $C_1$-$C_{18}$ alkyl, $C_2$-$C_{20}$ alkenyl, $C_2$-$C_{20}$ alkynyl, methyl, ethyl, perfluorinated methyl, and perfluorinated ethyl, which $C_1$-$C_{18}$ alkyl, $C_2$-$C_{20}$ alkenyl, $C_2$-$C_{20}$ alkynyl, methyl, or ethyl can optionally be substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, perfluorinated ethyl, $C_1$-$C_4$ alkoxy, $C_2$-$C_4$ alkanoyl (—CO—($C_2$-$C_4$ alkyl)), $C_2$-$C_4$ alkanoyloxy (—CO—O—($C_2$-$C_4$ alkyl)), $C_2$-$C_4$ alkoxycarbonyl (—O—CO—($C_2$-$C_4$ alkyl)), nitro, amino, mono($C_1$-$C_4$ alkyl)amino, di($C_1$-$C_4$ alkyl)amino, $C_1$-$C_4$ alkylthio (—S—($C_1$-$C_4$ alkyl)), $C_1$-$C_4$ alkylsulfinyl (—SO—($C_1$-$C_4$ alkyl)), $C_1$-$C_4$ alkylsulfonyl (—S(=O)$_2$-($C_1$-$C_4$ alkyl)), oxo (=O), thioxo (=S), or $C_1$-$C_4$ alkanoylamino (—CO—NH—($C_1$-$C_4$ alkyl)).

12. The compound of claim 1, wherein $R^5$, $R^6$, and $R^7$ are the same or different and each is independently selected from methyl, ethyl, propyl, butyl, pentyl, and hexyl.

13. The compound of claim 1, wherein $R^4$ is

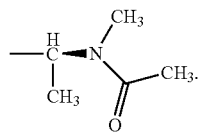

14. The compound of claim 1, wherein m is 1, 2, 3, 4, or 5.

15. The compound of claim 1, wherein Z is BSA, CSA, HSA, FSA or ESA.

16. The compound of claim 1, wherein the compound is

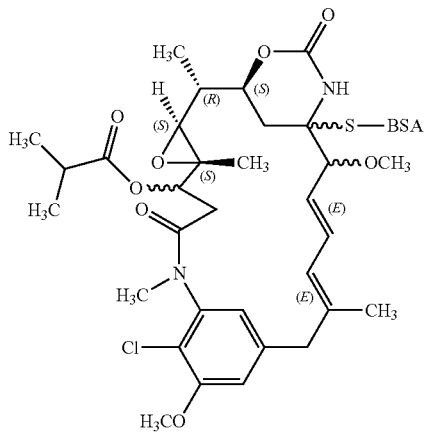

where the Human Serum Albumin (HSA) is attached via its cys-34 thiol, where the Bovine Serum Albumin (BSA) is attached via its cys-34 thiol,

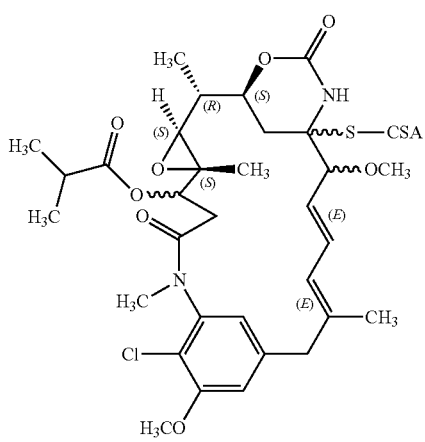

where the Canine Serum Albumin (CSA) is attached via its cys-34 thiol, where the Feline Serum Albumin (FSA) is attached via its cys-34 thiol,

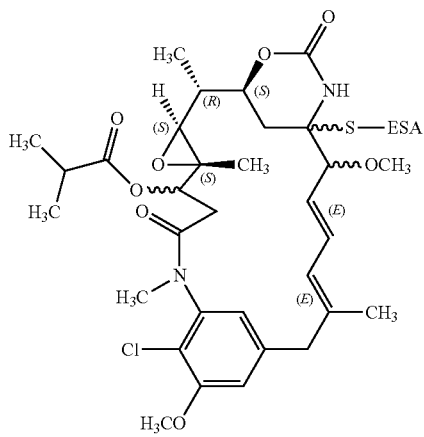

where the Equine Serum Albumin (ESA) is attached via its cys-34 thiol,

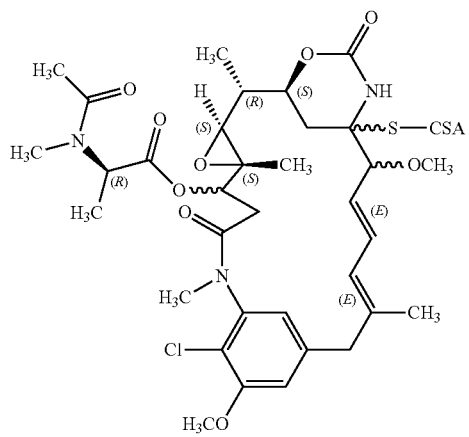

where the Canine Serum Albumin (CSA) is attached via its cys-34 thiol,

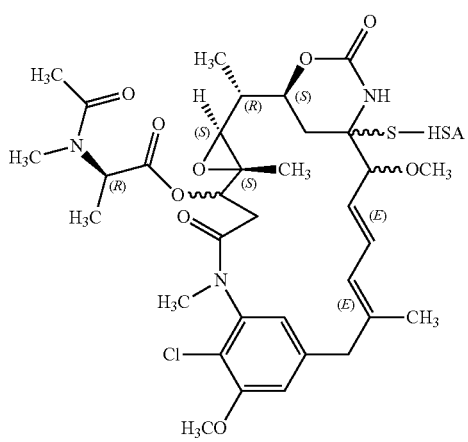

where the Human Serum Albumin (HSA) is attached via its cys-34 thiol,

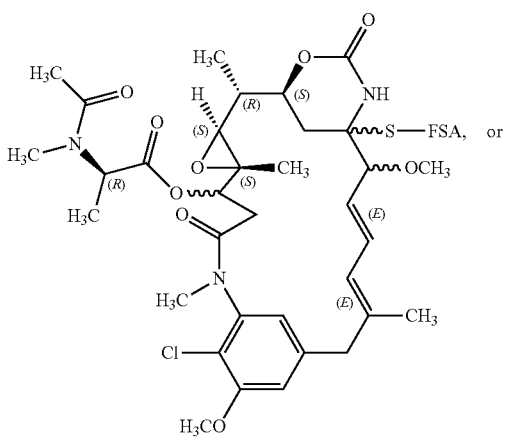

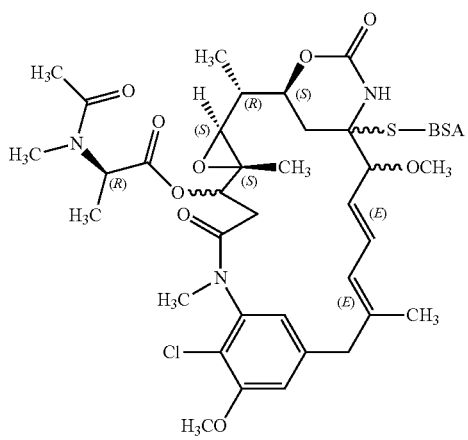

where the Bovine Serum Albumin (BSA) is attached via its cys-34 thiol,

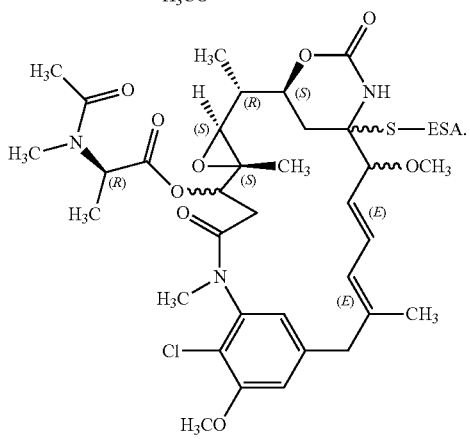

17. A composition comprising a compound of claim 1.

18. A pharmaceutical composition comprising a compound of claim 1.

19. A method for providing an animal with the compound of claim 1 comprising one or more administrations of one or more compositions comprising the compound of claim 1, wherein the compositions may be the same or different if there is more than one administration.

20. A method for treating an animal for a disease, comprising one or more administrations of one or more compositions comprising the compound of claim 1, wherein the compositions may be the same or different if there is more than one administration.

21. The method of claim 20, wherein at least one of the one or more administrations comprises parenteral administration, a mucosal administration, intravenous administration, subcutaneous administration, topical administration, intradermal administration, oral administration, sublingual administration, intranasal administration, or intramuscular administration.

22. The method of claim 20, wherein the animal is a human, a canine, a primate, a feline, a bovine, or an equine.

23. The method of claim 20, wherein the animal is in need of the treatment.

24. The method of claim 20, wherein the method is for treating cancer.

25. The method of claim 20, wherein the method is for treating acute lymphoblastic leukemia, astrocytoma, basal cell carcinoma, bladder cancer, bone marrow cancer, breast cancer, chronic lymphocytic leukemia (CLL), CNS cancer, colon cancer, colorectal cancer, endometrial cancer, gastric cancer, glioblastoma, glioblastoma multiforme, glioma, gliosarcoma, head and neck cancers, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, cancers that can result in metastasis, cancers resulting from metastasis, or cancerous tumors thereof.

26. The method of claim 20, wherein the method is for treating basal cell carcinoma, bladder cancer, bone marrow cancer, breast cancer, CNS cancer, colon cancer, colorectal cancer, endometrial cancer, gastric cancer, glioblastoma, glioblastoma multiforme, glioma, gliosarcoma, head and neck cancers, hepatocellular carcinoma, kidney cancer, leukemia, liver cancer, lung cancer, lymphoma, melanoma, malignant nerve sheath tumors, medulloblastoma, meningioma, multiple myeloma, nasopharyngeal carcinoma, neuroblastoma, non-Hodgkin lymphoma, non-small cell lung cancer, oral cancer, ovarian cancer, pancreatic cancer, prostate cancer, rectal cancer, renal cancer, renal cell carcinoma, rhabdomyosarcoma, squamous cell carcinoma, stomach cancer, thyroid cancer, uterine cancer, or cancerous tumors thereof.

27. The method of claim 20, wherein the method is for treating cancerous tumors.

28. The method of claim 20, wherein the method is for treating breast cancer, head and neck cancer, lung cancer, non-small cell lung cancer, lymphoma, ovarian cancer, or renal cancer.

29. A method for preparing a compound of claim 1 comprising, (a) reacting Z with a disulfide to provide activated Z;
  (b) reacting activated Z with Formula (II) to provide the compound; and
  (c) optionally, recovering the compound;
wherein
the Formula (II) is

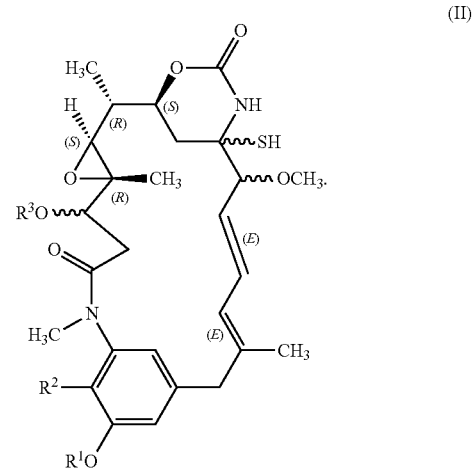

(II)

30. The method of claim 29, wherein the disulfide is at a concentration that is in mole equivalent excess of Z.

31. The method of claim 29, wherein the pH of the reaction solution in step (b) is from about 1.0 to about 7.0.

32. The method of claim 29, wherein the method further comprises lyophilization, after step (c) where step (c) is not optional or after step (b).

* * * * *